US011129851B2

(12) United States Patent
Simón et al.

(10) Patent No.: US 11,129,851 B2
(45) Date of Patent: Sep. 28, 2021

(54) STEM CELL THERAPY IN ENDOMETRIAL PATHOLOGIES

(71) Applicant: Igenomix S.L., Valencia (ES)

(72) Inventors: Carlos Simón, Valencia (ES); Xavier Santamaria, Barcelona (ES); Irene Cervelló, Paterna (ES); Antonio Pellicer, Paterna (ES)

(73) Assignee: IGENOMIX S.L., Valencia (ES)

( * ) Notice: Subject to any disclaimer, the term of this patent is extended or adjusted under 35 U.S.C. 154(b) by 35 days.

(21) Appl. No.: 15/318,825

(22) PCT Filed: Jun. 5, 2015

(86) PCT No.: PCT/IB2015/001715
§ 371 (c)(1),
(2) Date: Dec. 14, 2016

(87) PCT Pub. No.: WO2015/193737
PCT Pub. Date: Dec. 23, 2015

(65) Prior Publication Data
US 2017/0128492 A1 May 11, 2017

Related U.S. Application Data

(60) Provisional application No. 62/013,121, filed on Jun. 17, 2014.

(51) Int. Cl.
*A61K 35/28* (2015.01)
*A61K 9/00* (2006.01)
*C12N 5/0775* (2010.01)
*A61K 35/12* (2015.01)

(52) U.S. Cl.
CPC ............ *A61K 35/28* (2013.01); *A61K 9/0019* (2013.01); *C12N 5/0663* (2013.01); *A61K 2035/124* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 6,733,962 B2 | 5/2004 | Kliman et al. | |
| 2003/0077589 A1 | 4/2003 | Hess-Stumpp et al. | |
| 2003/0125282 A1 | 7/2003 | Weiss et al. | |
| 2003/0186300 A1 | 10/2003 | Akoum | |
| 2003/0228636 A1 | 12/2003 | Lessey | |
| 2004/0005612 A1 | 1/2004 | Guidice et al. | |
| 2005/0026891 A1 | 2/2005 | Hillisch et al. | |
| 2005/0032111 A1 | 2/2005 | MacCalman et al. | |
| 2005/0106134 A1 | 5/2005 | Nie et al. | |
| 2008/0245371 A1* | 10/2008 | Gruber .................. | A61B 1/303 128/831 |
| 2009/0111140 A1* | 4/2009 | Liu ..................... | A61K 49/1866 435/29 |
| 2010/0249015 A1* | 9/2010 | Martin ................ | A61K 38/1866 514/1.1 |
| 2012/0040849 A1 | 2/2012 | Vallés et al. | |
| 2012/0269774 A1* | 10/2012 | Ichim .................... | A61K 35/28 424/93.7 |
| 2013/0144114 A1 | 6/2013 | Vallés et al. | |
| 2017/0097358 A1 | 4/2017 | Simón et al. | |
| 2017/0128492 A1 | 5/2017 | Simón et al. | |

FOREIGN PATENT DOCUMENTS

| | | |
|---|---|---|
| EP | 1 016 410 A1 | 7/2000 |
| JP | 2005-539016 A | 12/2005 |
| JP | 2007-504807 A | 3/2007 |
| JP | 2007-278750 A | 10/2007 |
| JP | 2008-501035 A | 1/2008 |
| RU | 2515475 C1 | 10/2014 |
| WO | WO 90/13299 A1 | 11/1990 |
| WO | WO 01/89548 A2 | 11/2001 |
| WO | WO 03/062832 A1 | 7/2003 |
| WO | WO 2004/014935 A1 | 2/2004 |
| WO | WO 2004/058999 A2 | 7/2004 |
| WO | WO 2005/018796 A1 | 3/2005 |
| WO | WO 2005/026324 A2 | 3/2005 |
| WO | WO 2005/061725 A1 | 7/2005 |
| WO | WO 2005/117979 A2 | 12/2005 |
| WO | WO 2009/143633 A1 | 12/2009 |
| WO | WO 2013/057316 A2 | 4/2013 |
| WO | WO 2013/081554 A1 | 6/2013 |
| WO | WO 2013166281 * | 11/2013 |
| WO | WO 2014/001244 A1 | 1/2014 |

OTHER PUBLICATIONS

Mambelli et al., "A novel strategy of mesenchymal stem cells delivery in the uterus of mares with endometrosis", Theriogenology, 2013, vol. 79, pp. 744-750. (Year: 2013).*
Margalioth et al., "Investigation and treatment of repeated implantation failure following IVF-ET", Human Reproduction 2006, vol. 21, No. 12, pp. 3036-3043 (Year: 2006).*
International Search Report and Written Opinion for Application No. PCT/EP2011/050867 dated Apr. 19, 2011.
International Preliminary Report on Patentability for Application No. PCT/EP2011/050867 dated Aug. 2, 2012.
International Search Report and Written Opinion for Application No. PCT/ES2008/000513 dated Mar. 23, 2009.
International Preliminary Report on Patentability for Application No. PCT/ES2008/00513 dated Mar. 8, 2011.
International Search Report and Written Opinion for Application No. PCT/ES2009/000386 dated Dec. 11, 2009.
International Preliminary Report on Patentability for Application No. PCT/ES2009/000386 dated Oct. 4, 2010.

(Continued)

*Primary Examiner* — Laura Schuberg
(74) *Attorney, Agent, or Firm* — Wolf, Greenfield & Sacks, P.C.

(57) ABSTRACT

The invention generally relates to the ability of autologous CD133+ bone marrow stem cells (BMDSC) to induce endometrial regeneration and treat endometrial pathologies such as Asherman's syndrome and endometrial atrophy. Methods to induce endometrial regeneration are provided, which comprises administering an effective amount of autologous CD133$^+$ bone marrow derived stem cells (BMDSC) into uterine arteries of a subject in need thereof to induce endometrial regeneration.

20 Claims, 10 Drawing Sheets

(56) References Cited

OTHER PUBLICATIONS

International Search Report and Written Opinion dated Nov. 19, 2015 for Application No. PCT/IB2015/001404.
International Preliminary Report on Patentability dated Sep. 29, 2016 for Application No. PCT/IB2015/001404.
International Search Report and Written Opinion for PCT/IB2015/001715 dated Nov. 23, 2015.
International Preliminary Report on Patentability for PCT/IB2015/0001715 dated Dec. 29, 2016.
Partial European Search Report for Application No. EP 10382011.4 dated Jul. 9, 2010.
Extended European Search Report for Application No. EP 10382011.4 dated Sep. 29, 2010.
Extended European Search Report for Application No. EP 09800092.0 dated Feb. 10, 2012.
[No Author Listed], Agilent 012391 Whole Genome Oligo Microarray G4112A (Feature Number Version). Agilent Technologies. GEO. Nov. 17, 2004[2 pages]. http://www.ncbi.nlm.nih.gov/geo/query/acc.cgi?acc=GPL1708. [last accessed Jan. 30, 2009].
[No Author Listed], Report of the National High Blood Pressure Education Program Working Group on High Blood Pressure in Pregnancy. Am J Obstet Gynecol. Jul. 2000;183(1):S1-S22. Abstract Only.
Achache et al., Endometrial receptivity markers, the journey to successful embryo implantation. Hum Reprod Update. Nov.-Dec. 2006;12(6):731-46. Epub Sep. 18, 2006.
Agbulut et al., Comparison of human skeletal myoblasts and bone marrow-derived CD133+ progenitors for the repair of infarcted myocardium. J Am Coll Cardiol. Jul. 21, 2004;44(2):458-63.
Aghajanova et al., The bone marrow-derived human mesenchymal stem cell: potential progenitor of the endometrial stromal fibroblast. Biol Reprod. Jun. 2010;82(6):1076-87. doi: 10.1095/biolreprod.109.082867. Epub Feb. 10, 2010. Erratum in: Biol Reprod. May 2015;92(5):126.
Alawadhi et al., Bone Marrow-Derived Stem Cell (BMDSC) transplantation improves fertility in a murine model of Asherman's syndrome. PLoS One. May 12, 2014;9(5):e96662. doi: 10.1371/journal.pone.0096662. eCollection 2014.
Al-Shahrour et al., BABELOMICS: a systems biology perspective in the functional annotation of genome-scale experiments. Nucleic Acids Res. Jul. 1, 2006;34(Web Server issue):W472-6.
Al-Shahrour et al., FatiGO +: a functional profiling tool for genomic data. Integration of functional annotation, regulatory motifs and interaction data with microarray experiments. Nucleic Acids Res. Jul. 2007;35(Web Server issue):W91-6.
Al-Shahrour et al., FatiGO: a web tool for finding significant associations of Gene Ontology terms with groups of genes. Bioinformatics. Mar. 1, 2004;20(4):578-80.
Al-Shahrour et al., From genes to functional classes in the study of biological systems. BMC Bioinformatics. Apr. 3, 2007;8:114.
Am Esch et al., Infusion of CD133+ bone marrow-derived stem cells after selective portal vein embolization enhances functional hepatic reserves after extended right hepatectomy: a retrospective single-center study. Ann Surg. Jan. 2012;255(1):79-85. doi: 10.1097/SLA.0b013e31823d7d08.
Arnesen et al., Increased fibrinolytic activity after surgery induced by low dose heparin. Thromb Res. 1987; 45: 553-559. Abstract Only.
Asherman, Amenorrhoea traumatica (atretica). J Obstet Gynecol Br Emp. Feb. 1948;55(1):23-30.
Balasch et al., The usefulness of endometrial biopsy for luteal phase evaluation in infertility. Hum Reprod. Aug. 1992;7(7):973-7.
Barbash et al., Systemic delivery of bone marrow-derived mesenchymal stem cells to the infarcted myocardium: feasibility, cell migration, and body distribution. Circulation. Aug. 19, 2003;108(7):863-8. Epub Aug. 4, 2003.
Bastani et al., Determination of 8-epi PGf(2alpha) concentrations as a biomarker of oxidative stress using triple-stage liquid chromatography/tandem mass spectrometry. Rapid Commun Mass Spectrom. Sep. 2009;23(18):2885-90.
Batista et al., Midluteal phase endometrial biopsy does not accurately predict luteal function. Fertil Steril. Feb. 1993;59(2):294-300.
Beier et al., Plasminogen activator inhibitor-1 deficient mice are protected from angiotensin II-induced fibrosis. Arch Biochem Biophys. Jun. 1, 2011;510(1):19-26. doi: 10.1016/j.abb.2011.04.001. Author manuscript.
Belotti et al., Full GMP-compliant validation of bone marrow-derived human CD133(+) cells as advanced therapy medicinal product for refractory ischemic cardiomyopathy. Biomed Res Int. 2015;2015:473159. doi: 10.1155/2015/473159. Epub Oct. 1, 2015.
Benjamini et al., Controlling the false discovery rate: a practical and powerful approach to multiple testing. J Royal Statist Soc B 1995; 57: 289-300.
Bharadwaj et al., Annexin A2 heterotetramer: structure and function. Int J Mol Sci Mar. 19, 2013;14(3):6259-305. doi: 10.3390/ijms14036259.
Bongiovanni et al., The CD133+ cell as advanced medicinal product for myocardial and limb ischemia. Stem Cells Dev. Oct. 15, 2014;23(20):2403-21. doi: 10.1089/scd.2014.0111. Epub Aug. 20, 2014.
Boomsma et al., Cytokine profiling in endometrial secretions: a non-invasive window on endometrial receptivity. Reprod Biomed Online. Jan. 2009;18(1):85-94.
Borthwick et al., Determination of the Transcript Profile of Human Endometrium. Molecular Human Reproduction. 2003;9(1):19-33.
Boyd et al., Associations of personal and family preeclampsia history with the risk of early-, intermediate- and late-onset preeclampsia. Am J Epidemiol. Dec. 1, 2013;178(11):1611-9. doi: 10.1093/aje/kwt189.
Bradley et al., Transcatheter uterine artery embolisation to treat large uterine fibroids. Br J Obstet Gynaecol. Feb. 1998;105(2):235-40.
Brar et al., Progesterone-dependent decidualization of the human endometrium is mediated by cAMP. Endocrine. Jun. 1997;6(3):301-7. Abstract Only.
Bratincsák et al., CD45-positive blood cells give rise to uterine epithelial cells in mice. Stem Cells. Nov. 2007;25(11):2820-6. Epub Jul. 26, 2007.
Brosens et al., The role of the spiral arteries in the pathogenesis of preeclampsia. Obstet Gynecol Annu. 1972;1:177-91.
Brown et al., Endometrial glycodelin-A expression in the luteal phase of stimulated ovarian cycles. Fertil Steril. Jul. 2000;74(1):130-3.
Brumsted et al., Prostaglandin F2 alpha synthesis and metabolism by luteal phase endometrium in vitro. Fertil Steril. Nov. 1989;52(5):769-73.
Burney et al., Gene Expression Analysis of Endometrium Reveals Progesterone Resistance and Candidate Susceptibility Genes in Women with Endometriosis. Endocrinology. Aug. 2007;148(8):3814-26. Epub May 17, 2007.
Burton et al., Human early placental development: potential roles of the endometrial glands. Placenta. Apr. 2007;28 Suppl A:S64-9. Epub Mar. 8, 2007.
Cañas et al., Annexin A2 autoantibodies in thrombosis and autoimmune diseases. Thromb Res. Feb. 2015;135(2):226-30. doi: 10.1016/j.thromres.2014.11.034. Epub Dec. 13, 2014.
Capella-Allouc et al., Hysteroscopic treatment of severe Asherman's syndrome and subsequent fertility. Hum Reprod. May 1999;14(5):1230-3.
Carson et al., Changes in Gene Expression During the Early to Mid-Luteal (Receptive Phase) Transition in Human Endometrium Detected by High-Density Microarray Screening. Mol Hum Reprod. Sep. 2002;8(9):871-9.
Casado-Vela et al., Comprehensive Proteomic Analysis of Human Endometrial Fluid Aspirate. Journal of Proteome Research. 2009;8:4622-4632.
Catalano et al., The effect of RU486 on the gene expression profile in an endometrial explant model. Mol Hum Reprod. Aug. 2003;9(8):465-73.

(56) References Cited

OTHER PUBLICATIONS

Cervelló et al., Bone marrow-derived cells from male donors do not contribute to the endometrial side population of the recipient. PLoS One. 2012;7(1):e30260. doi: 10.1371/journal.pone.0030260. Epub Jan. 19, 2012.
Cervelló et al., Cell Therapy and Tissue Engineering from and toward the Uterus. Semin Reprod Med. Sep. 2015;33(5):366-72. doi: 10.1055/s-0035-1559581. Epub Aug. 18, 2015.
Cervelló et al., Human CD133+ bone marrow-derived stem cells promote endometrial proliferation in a murine model of Asherman syndrome. Fertil Steril. Dec. 2015;104(6):1552-60.e1-3. doi: 10.1016/j.fertnstert.2015.08.032.
Cervelló et al., Human endometrial side population cells exhibit genotypic, phenotypic and functional features of somatic stem cells. PLoS One. Jun. 24, 2010;5(6):e10964. doi: 10.1371/journal.pone.0010964.
Cervelló et al., Reconstruction of endometrium from human endometrial side population cell lines. PLoS One. 2011;6(6):e21221. doi: 10.1371/journal.pone.0021221. Epub Jun. 21, 2011.
Cesarman et al., An endothelial cell receptor for plasminogen/tissue plasminogen activator (t-PA). II. Annexin II-mediated enhancement of t-PA-dependent plasminogen activation. J Biol Chem. Aug. 19, 1994;269(33):21198-203.
Cesarman-Maus et al., Autoantibodies against the fibrinolytic receptor, annexin 2, in antiphospholipid syndrome. Blood. Jun. 1, 2006;107(11):4375-82.
Cesarman-Maus et al., Molecular mechanisms of fibrinolysis. Br J Haematol. May 2005;129(3):307-21.
Cha et al., Molecular Interplay in Successful Implantation. Ten Critical Topics in Reproductive Medicine. Science/AAAS. 2013:44-48. doi: 10.1126/science.342.6164.1393-o.
Chartrand et al., Effect of dietary fat sources on systemic and intrauterine synthesis of prostaglandins during early pregnancy in gilts. J Anim Sci. Mar. 2003;81(3):726-34.
Cho et al., Lifetime expression of stem cell markers in the uterine endometrium. Fertil Steril. Feb. 2004;81(2):403-7.
Chu et al., Urokinase-type plasminogen activator, receptor, and inhibitor correlating with gelatinase-B (MMP-9) contribute to inflammation in gouty arthritis of the knee. J Rheumatol. Feb. 2006;33(2):311-7. Abstract Only.
Conserva et al., Recurrence and severity of abnormal pregnancy outcome in patients treated by low-molecular-weight heparin: a prospective pilot study. J Matern Fetal Neonatal Med. Aug. 2012;25(8):1467-73. doi: 10.3109/14767058.2011.643326.
Coutifaris et al., Histological dating of timed endometrial biopsy tissue is not related to fertility status. Fertil Steril. Nov. 2004;82(5):1264-72.
Crabbe et al., Tissue plasminogen activator: a new thrombolytic agent. Clin Pharm. May 1987;6(5):373-86. Review. Erratum in: Clin Pharm Dec. 1987;6(12):925. Abstract Only.
Creus et al., alphavbeta3 integrin expression and pinopod formation in normal and out-of-phase endometria of fertile and infertile women. Hum Reprod. Sep. 2002;17(9):2279-86.
Díaz-Gimeno et al., A genomic diagnostic tool for human endometrial receptivity based on the transcriptomic signature. Fertil Steril. Jan. 2011;95(1):50-60. Epub Jul. 8, 2010.
Dimitrov et al., Characterization of clonogenic stromal cells isolated from human endometrium. Reproduction. Apr. 2008;135(4):551-8. doi: 10.1530/REP-07-0428.
Dmowski et al., Asherman's syndrome and risk of placenta accreta. Obstet Gynecol. Aug. 1969;34(2):288-99.
Dome et al., Circulating bone marrow-derived endothelial progenitor cells: characterization, mobilization, and therapeutic considerations in malignant disease. Cytometry A. Mar. 2008;73(3):186-93.
Domínguez et al., Proteomic analysis of the human receptive versus non-receptive endometrium using differential in-gel electrophoresis and MALDI-MS unveils stathmin 1 and annexin A2 as differentially regulated. Hum Reprod. Oct. 2009;24(10):2607-17. doi: 10.1093/humrep/dep230.
Downie et al., Levels of prostaglandins in human endometrium during the normal menstrual cycle. J Physiol. Jan. 1974;236(2):465-72.
Du et al., Contribution of bone marrow-derived stem cells to endometrium and endometriosis. Stem Cells. Aug. 2007;25(8):2082-6. Epub Apr. 26, 2007.
Du et al., Ischemia/reperfusion injury promotes and granulocyte-colony stimulating factor inhibits migration of bone marrow-derived stem cells to endometrium. Stem Cells Dev. Dec. 10, 2012;21(18):3324-31. doi: 10.1089/scd.2011.0193. Epub Aug. 16, 2012.
Dunn et al., Decidualization of the human endometrial stromal cell: an enigmatic transformation. Reprod Biomed Online. Sep. 2003;7(2):151-61. Abstract Only.
European IVF-Monitoring Consortium (EIM) for the European Society of Human Reproduction and Embryology (ESHRE) et al., Assisted reproductive technology in Europe, 2012: results generated from European registers by ESHRE. Hum Reprod. Aug. 2016;31(8):1638-52. doi: 10.1093/humrep/dew151. Epub Jun. 19, 2016.
Fadini et al., Critical reevaluation of endothelial progenitor cell phenotypes for therapeutic and diagnostic use. Circ Res. Feb. 17, 2012;110(4):624-37. doi: 10.1161/CIRCRESAHA.111.243386.
Farhi et al., Induced regeneration of endometrium following curettage for abortion: a comparative study. Hum Reprod. Jul. 1993;8(7):1143-4.
Flores-Ramírez et al., Intracoronary infusion of CD133+ endothelial progenitor cells improves heart function and quality of life in patients with chronic post-infarct heart insufficiency. Cardiovasc Revasc Med. Apr.-Jun. 2010;11(2):72-8. doi: 10.1016/j.carrev.2009.04.001.
Founds et al., Altered global gene expression in first trimester placentas of women destined to develop preeclampsia. Placenta. Jan. 2010 ;30(1):15-24. doi: 10.1016/j.placenta.2008.09.015. Epub Nov. 21, 2008 . Author manuscript.
Freund et al., Comparative analysis of proliferative potential and clonogenicity of MACS-immunomagnetic isolated CD34+ and CD133+ blood stem cells derived from a single donor. Cell Prolif. Aug. 2006;39(4):325-32.
Friel et al., Epigenetic regulation of CD133 and tumorigenicity of CD133 positive and negative endometrial cancer cells. Reprod Biol Endocrinol. Dec. 1, 2010;8:147. doi: 10.1186/1477-7827-8-147.
Fürst et al., Portal vein embolization and autologous CD133+ bone marrow stem cells for liver regeneration: initial experience. Radiology. Apr. 2007;243(1):171-9. Epub Feb. 20, 2007.
Gargett et al., Adult stem cells in the endometrium. Mol Hum Reprod. Nov. 2010;16(11):818-34. doi: 10.1093/molehr/gaq061. Epub Jul. 13, 2010.
Gargett et al., Generating receptive endometrium in Asherman's syndrome. J Hum Reprod Sci. Jan. 2011;4(1):49-52.
Gargett et al., Isolation and culture of epithelial progenitors and mesenchymal stem cells from human endometrium. Biol Reprod. Jun. 2009;80(6):1136-45. doi:10.1095/biolreprod.108.075226. Epub Feb. 18, 2009.
Garrido-Gómez et al., Annexin A2 is critical for embryo adhesiveness to the human endometrium by RhoA activation through F-actin regulation. FASEB J. Sep. 2012 ;26(9):3715-27. doi: 10.1096/fj.12-204008. Abstract Only.
Garrido-Gomez et al., Modeling human endometrial decidualization from the interaction between proteome and secretome. J Clin Endocrinol Metab. Mar. 2011;96(3):706-16. doi: 10.1210/jc.2010-1825.
Gellersen et al., Invasiveness of human endometrial stromal cells is promoted by decidualization and by trophoblast-derived signals. Hum Reprod. Apr. 2010;25(4):862-73. doi:10.1093/humrep/dep468.
Gemzell-Danielsson et al., The effect of antiprogestin (RU 486) and prostaglandin biosynthesis inhibitor (naproxen) on uterine fluid prostaglandin F2 alpha concentrations. Hum Reprod. Sep. 1994;9(9):1626-30.

(56) References Cited

OTHER PUBLICATIONS

Giudice et al., Paracrine actions of insulin-like growth factors and IGF binding protein-1 in non-pregnant human endometrium and at the decidual-trophoblast interface. J Reprod Immunol. Aug. 1998;39(1-2):133-48. Abstract Only.
Giudice, Potential biochemical markers of uterine receptivity. Hum Reprod. Dec. 1999;14 Suppl 2:3-16.
Gohil et al., The genetics of venous thromboembolism. A meta-analysis involving approximately 120,000 cases and 180,000 controls. Thromb Haemost. Aug. 2009;102(2):360-70. doi: 10.1160/TH09-01-0013. Abstract Only.
Goodwin et al., Uterine artery embolization for treatment of leiomyomata: long-term outcomes from the FIBROID Registry. Obstet Gynecol. Jan. 2008;111(1):22-33. doi: 10.1097/01.AOG.0000296526.71749.c9n.
Gordon et al., Large-scale isolation of CD133+ progenitor cells from G-CSF mobilized peripheral blood stem cells. Bone Marrow Transplant. Jan. 2003;31(1):17-22.
Goussetis et al., Intracoronary infusion of CD133+ and CD133-CD34+ selected autologous bone marrow progenitor cells in patients with chronic ischemic cardiomyopathy: cell isolation, adherence to the infarcted area, and body distribution. Stem Cells. Oct. 2006;24(10):2279-83. Epub Jun. 22, 2006.
Gray et al., Evidence that absence of endometrial gland secretions in uterine gland knockout ewes compromises conceptus survival and elongation. Reproduction. Aug. 2002;124(2):289-300.
Handgretinger et al., Biology and plasticity of CD133$^+$ hematopoietic stem cells. Ann NY Acad Sci. May 2003;996:141-51.
Handgretinger et al., CD133-Positive Hematopoietic Stem Cells: From Biology to Medicine. Adv Exp Med Biol. 2013;777:99-111. doi: 10.1007/978-1-4614-5894-4_7.
Haus et al., CD133-enriched Xeno-Free human embryonic-derived neural stem cells expand rapidly in culture and do not form teratomas in immunodeficient mice. Stem Cell Res. Sep. 2014;13(2):214-26. doi: 10.1016/j.scr.2014.06.008.
Herrero et al., a hierarchical unsupervised growing neural network for clustering gene expression patterns. Bioinformatics. Feb. 2001;17(2):126-36.
Hida et al., Novel cardiac precursor-like cells from human menstrual blood-derived mesenchymal cells. Stem Cells. Jul. 2008;26(7):1695-704. doi: 10.1634/stemcells.2007-0826. Epub Apr. 17, 2008.
Hoozemans et al., Human embryo implantation: current knowledge and clinical implications in assisted reproductive technology. Reprod Biomed Online. Dec. 2004;9(6):692-715.
Horcajadas et al., Effect of an Intrauterine Device on the Gene Expression Profile of the Endometrium. J Clin Endocrinol Metab. Aug. 2006;91(8):3199-207. Epub May 30, 2006.
Horcajadas et al., Effect of Controlled Ovarian Hyperstimulation in IVF on Endometrial Gene Expression Profiles. Mol Hum Reprod. Mar. 2005;11(3):195-205. Epub Feb. 4, 2005.
Horcajadas et al., Wide genomic analysis of human endometrial receptivity: new times, new opportunities. Hum Reprod Update. Jan.-Feb. 2007;13(1):77-86. Epub Sep 7, 2006.
Ikoma et al., Bone marrow-derived cells from male donors can compose endometrial glands in female transplant recipients. Am J Obstet Gynecol. Dec. 2009;201(6):608.e1-8. doi:10.1016/j.ajog.2009.07.026. Epub Oct. 3, 2009.
Irollo et al., CD133: to be or not to be, is this the real question? Am J Transl Res. Sep. 25, 2013;5(6):563-81.
Irwin et al., Sex steroids and growth factors differentially regulate the growth and differentiation of cultured human endometrial stromal cells. Endocrinology. Nov. 1991;129(5):2385-92. Abstract Only.
Ishihara et al., Metabolism of arachidonic acid and synthesis of prostanoids in human endometrium and decidua. Prostaglandins Leukot Med. Sep. 1986;24(1):93-102.
Jabbour et al., Potential roles of decidual prolactin in early pregnancy. Reproduction. Feb. 2001;121(2):197-205.
Jaime-Pérez et al., Assessment of immune reconstitution status in recipients of a successful hematopoietic stem cell transplant from peripheral blood after reduced intensity conditioning. Blood Cells Mol Dis. May 2016;58:52-6. doi: 10.1016/j.bcmd.2016.03.001. Epub Mar 3, 2016.
Jensen et al., Prostaglandins in the menstrual cycle of women. A review. Dan Med Bull. Jun. 1987;34(3):178-82.
Jimenez-Quevedo et al., Selected CD133$^+$ progenitor cells to promote angiogenesis in patients with refractory angina: final results of the PROGENITOR randomized trial. Circ Res. Nov. 7, 2014;115(11):950-60. doi: 10.1161/CIRCRESAHA.115.303463. Epub Sep. 17, 2014.
Jing et al., Rat bone marrow mesenchymal stem cells improve regeneration of thin endometrium in rat. Fertil Steril. Feb. 2014;101(2):587-94. doi: 10.1016/j.fertnstert.2013.10.053. Epub Dec. 17, 2013.
Kamei et al., Ex-vivo expanded human blood-derived CD133+ cells promote repair of injured spinal cord. J Neurol Sci. May 15, 2013;328(1-2):41-50. doi: 10.1016/j.jns.2013.02.013.
Kato et al., Characterization of side-population cells in human normal endometrium. Hum Reprod. May 2007;22(5):1214-23. Epub Feb. 5, 2007.
Kelly et al., The relationship between menstrual blood loss and prostaglandin production in the human: evidence for increased availability of arachidonic acid in women suffering from menorrhagia. Prostaglandins Leukot Med. Oct. 1984;16(1):69-78.
Kijima et al., Regeneration of peripheral nerve after transplantation of CD133$^+$ cells derived from human peripheral blood. J Neurosurg. Apr. 2009;110(4):758-67. doi: 10.3171/2008.3.17571.
Kliman et al., Optimization of endometrial preparation results in a normal endometrial function test (EFT) and good reproductive outcome in donor ovum recipients. J Assist Reprod Genet. Jul.-Aug. 2006;23(7-8):299-303. Epub Sep. 17, 2006.
Kordes et al., CD133+ hepatic stellate cells are progenitor cells. Biochem Biophys Res Commun. Jan. 12, 2007;352(2):410-7. Epub Nov. 15, 2006.
Kruse-Blinkenberg et al., The influence of low dose heparin in elective surgery on blood coagulation, fibrinolysis, platelet function, antithrombin Iii and antiplasmin. Acta Chir Scand. 1980;146(6):375-82. Abstract Only.
Lessey et al., Integrins as markers of uterine receptivity in women with primary unexplained infertility. Fertil Steril. Mar. 1995;63(3):535-42.
Lessey, Endometrial receptivity and the window of implantation. Baillieres Best Pract Res Clin Obstet Gynaecol. Oct. 2000;14(5):775-88.
Lessey, Two pathways of progesterone action in the human endometrium: implications for implantation and contraception. Steroids. Nov. 2003;68(10-13):809-15.
Li et al., How precise is histologic dating of endometrium using the standard dating criteria? Fertil Steril. May 1989;51(5):759-63.
Li, CD133: a stem cell biomarker and beyond. Exp Hematol Oncol. Jul. 1, 2013;2(1):17. doi: 10.1186/2162-3619-2-17.
Liew et al., Endothelial progenitor cells: diagnostic and therapeutic considerations. BioEssays. Mar. 2006;28(3):261-70.
Lim et al., Molecules in blastocyst implantation: uterine and embryonic perspectives. Vitam Horm. 2002;64:43-76.
Lim et al., Prostaglandin E2 receptor subtype EP2 gene expression in the mouse uterus coincides with differentiation of the luminal epithelium for implantation. Endocrinology. Nov. 1997;138(11):4599-606.
Ling et al., Annexin II regulates fibrin homeostasis and neoangiogenesis in vivo. J Clin Invest. Jan. 2004;113(1):38-48.
Ma et al., Intramyocardial delivery of human CD133+ cells in a SCID mouse cryoinjury model: Bone marrow vs. cord blood-derived cells. Cardiovasc Res. Jul. 1, 2006;71(1):158-69. Epub Apr. 3, 2006.
Maathuis et al., Concentrations of prostaglandins F2alpha and E2 in the endometrium throughout the human menstrual cycle, after the administration of clomiphene or an oestrogen-progestogen pill and in early pregnancy. J Endocrinol. Jun. 1978;77(3):361-71.
Maathuis, Cyclic changes in the concentration of prostaglandin F2alpha in human uterine flushings. Br J Obstet Gynaecol. Mar. 1978;85(3):207-10.

(56) References Cited

OTHER PUBLICATIONS

Manginas et al., Pilot study to evaluate the safety and feasibility of intracoronary CD133+ and CD133" CD34+ cell therapy in patients with nonviable anterior myocardial infarction. Catheter Cardiovasc Interv. May 1, 2007;69(6):773-81.

Manns et al., Prostaglandin Concentrations in Uterine Fluid of Cows with Pyometra. Can J Comp Med. 1985;49:436-438.

Mansour et al., COMPARE-AMI trial: comparison of intracoronary injection of CD133+ bone marrow stem cells to placebo in patients after acute myocardial infarction and left ventricular dysfunction: study rationale and design. J Cardiovasc Transl Res. Apr. 2010;3(2):153-9. doi: 10.1007/s12265-009-9145-2. Epub Nov. 12, 2009.

March, Management of Asherman's syndrome. Reprod Biomed Online. Jul. 2011;23(1):63-76. doi: 10.1016/j.rbmo.2010.11.018. Epub Dec. 4, 2010.

Masuda et al., Estrogen-mediated endothelial progenitor cell biology and kinetics for physiological postnatal vasculogenesis. Circ Res. Sep. 14, 2007;101(6):598-606. Epub Jul. 26, 2007.

Masuda et al., Stem cell-like properties of the endometrial side population: implication in endometrial regeneration. PLoS One. Apr. 28, 2010;5(4):e10387. doi: 10.1371/journal.pone.0010387.

Meng et al., Endometrial regenerative cells: a novel stem cell population. J Transl Med. Nov. 15, 2007;5:57.

Menkhorst et al., Decidual-secreted factors alter invasive trophoblast membrane and secreted proteins implying a role for decidual cell regulation of placentation. PLoS One. 2012;7(2):e31418. doi: 10.1371/journal.pone.0031418. Epub Feb. 16, 2012.

Meyer, Luteal versus placental progesterone: the situation in the cow, pig and bitch. Exp Clin Endocrinol. 1994;102(3):190-2. Biosis abstract accession No. PREV199497469780.

Mints et al., Endometrial endothelial cells are derived from donor stem cells in a bone marrow transplant recipient. Hum Reprod. Jan. 2008;23(1):139-43. Epub Nov. 2, 2007.

Mirkin et al., In search of candidate genes critically expressed in the human endometrium during the window of implantation. Hum Reprod. Aug. 2005;20(8):2104-17. Epub May 5, 2005.

Morelli et al., Experimental evidence for bone marrow as a source of nonhematopoietic endometrial stromal and epithelial compartment cells in a murine model. Biol Reprod. Jul. 11, 2013;89(1):7. doi: 10.1095/biolreprod.113.107987. Print Jul. 2013.

Murray et al., A critical analysis of the accuracy, reproducibility, and clinical utility of histologic endometrial dating in fertile women. Fertil Steril. May 2004;81(5):1333-43.

Musina et al., Endometrial mesenchymal stem cells isolated from the menstrual blood. Bull Exp Biol Med. Apr. 2008;145(4):539-43.

Mutlu et al., The endometrium as a source of mesenchymal stem cells for regenerative medicine. Biol Reprod. Jun. 2015;92(6):138. doi: 10.1095/biolreprod.114.126771. Epub Apr. 22, 2015.

Nagori et al., Endometrial regeneration using autologous adult stem cells followed by conception by in vitro fertilization in a patient of severe Asherman's syndrome. J Hum Reprod Sci. Jan. 2011;4(1):43-8. doi: 10.4103/0974-1208.82360.

Naicker et al., Quantitative analysis of trophoblast invasion in preeclampsia. Acta Obstet Gynecol Scand. Aug. 2003;82(8):722-9. Abstract Only.

Nasseri et al., Autologous CD133+ bone marrow cells and bypass grafting for regeneration of ischaemic myocardium: the Cardio133 trial. Eur Heart J. May 14, 2014;35(19):1263-74. doi: 10.1093/eurheartj/ehu007. Epub Feb. 3, 2014.

Nikas et al., Endometrial pinopodes: some more understanding on human implantation? Reprod Biomed Online. 2002;4 Suppl 3:18-23.

Noyes et al., Dating the endometrial biopsy. Fertil Steril. 1950;1(1):3-25.

Ordi et al., Within-subject between-cycle variability of histological dating, alpha v beta 3 integrin expression, and pinopod formation in the human endometrium. J Clin Endocrinol Metab. May 2003;88(5):2119-25.

Papanikolaou et al., Early and late ovarian hyperstimulation syndrome: early pregnancy outcome and profile. Hum Reprod. Mar. 2005;20(3):636-41. Epub Dec. 2, 2004.

Pijnenborg et al., Fetal-maternal conflict, trophoblast invasion, preeclampsia, and the red queen. Hypertens Pregnancy. 2008;27(2):183-96. doi: 10.1080/10641950701826711. Abstract Only.

Pistofidis et al., Comparison of Operative and Fertility Outcome Between Groups of Women with Intrauterine Adhesions after Adhesiolysis. J Am Assoc Gynecol Laparosc. Aug. 1996;3(4, Supplement):S40.

Pittenger et al., Multilineage potential of adult human mesenchymal stem cells. Science. Apr. 2, 1999;284(5411):143-7.

Pogliani et al., Low-dose heparin in thoracic surgery: effect on blood coagulation and fibrinolysis system. Thromb Res. Jul. 15, 1982;27(2):211-9. Abstract Only.

Pompilio et al., Direct minimally invasive intramyocardial injection of bone marrow-derived AC133+ stem cells in patients with refractory ischemia: preliminary results. Thorac Cardiovasc Surg. Mar. 2008;56(2):71-6. doi: 10.1055/s-2007-989351.

Ponnampalam et al., Molecular classification of human endometrial cycle stages by transcriptional profiling. Mol Hum Reprod. Dec. 2004;10(12):879-93. Epub Oct. 22, 2004.

Rabaglino et al., A bioinformatics approach reveals evidence for impaired endometrial maturation before and during early pregnancy in women who developed preeclampsia. Hypertension. Feb. 2015;65(2):421-9. doi: 10.1161/HYPERTENSIONAHA.114.04481. Epub Nov. 24, 2014. Erratum in: Hypertension. Jun. 2015;65(6):e46-7. Author manuscript.

Rafii et al., Therapeutic stem and progenitor cell transplantation for organ vascularization and regeneration. Nat Med. Jun. 2003;9(6):702-12.

Ramathal et al., Endometrial decidualization: of mice and men. Semin Reprod Med. Jan. 2010;28(1):17-26. doi: 10.1055/s-0029-1242989. Author manuscript.

Ravina et al., Arterial embolisation to treat uterine myomata. The Lancet. Sep. 9, 1995;346(8976):671-2.

Rees et al., Endometrial and myometrial prostaglandin release during the menstrual cycle in relation to menstrual blood loss. J Clin Endocrinol Metab. May 1984;58(5):813-8.

Reijnen et al., The antiadhesive agent sodium hyaluronate increases the proliferation rate of human peritoneal mesothelial cells. Fertil Steril. Jul. 2000;74(1):146-51.

Richardson et al., CD133, a novel marker for human prostatic epithelial stem cells. J Cell Sci. Jul. 15, 2004;117(Pt 16):3539-45. Epub Jun. 29, 2004.

Riesewijk et al., Gene expression profiling of human endometrial receptivity on days LH+2 versus LH+7 by microarray technology. Mol Hum Reprod. May 2003;9(5):253-64.

Robb et al., Leukemia inhibitory factor and interleukin-11: cytokines with key roles in implantation. J Reprod Immunol. Oct.-Nov. 2002;57(1-2):129-41.

Roberts et al., Preeclampsia: recent insights. Hypertension. Dec. 2005;46(6):1243-9.

Roberts et al., The placenta in pre-eclampsia and intrauterine growth restriction. J Clin Pathol. Dec. 2008;61(12):1254-60. doi: 10.1136/jcp.2008.055236. Abstract Only.

Saed et al., Hypoxia-induced irreversible up-regulation of type I collagen and transforming growth factor-beta1 in human peritoneal fibroblasts. Fertil Steril. Jul. 2002;78(1):144-7.

Sagrinati et al., Isolation and characterization of multipotent progenitor cells from the Bowman's capsule of adult human kidneys. J Am Soc Nephrol. Sep. 2006;17(9):2443-56. Epub Aug. 2, 2006.

Salle et al., Antibodies directed against annexin A2 and obstetric morbidity. J Reprod Immunol. Nov. 2016;118:50-53. doi: 10.1016/j.jri.2016.08.010.

Santamaria et al., Autologous cell therapy with CD133+ bone marrow-derived stem cells for refractory Asherman's syndrome and endometrial atrophy: a pilot cohort study. Hum Reprod. May 2016;31(5):1087-96. doi: 10.1093/humrep/dew/042. Epub Mar. 22, 2016.

Schmohl et al., CD133, Selectively Targeting the Root of Cancer. Toxins (Basel). May 28, 2016;8(6). pii: E165. doi: 10.3390/toxins8060165.

(56) References Cited

OTHER PUBLICATIONS

Schots et al., Evidence that intracoronary-injected CD133+ peripheral blood progenitor cells home to the myocardium in chronic postinfarction heart failure. Exp Hematol. Dec. 2007;35(12):1884-90. Epub Oct. 17, 2007.
Schwab et al., Co-expression of two perivascular cell markers isolates mesenchymal stem-like cells from human endometrium. Hum Reprod. Nov. 2007;22(11):2903-11. Epub Sep. 14, 2007.
Schwab et al., Putative stem cell activity of human endometrial epithelial and stromal cells during the menstrual cycle. Fertil Steril. Oct. 2005;84 Suppl 2:1124-30.
Senturk et al., Thin endometrium in assisted reproductive technology. Curr Opin Obstet Gynecol. Jun. 2008;20(3):221-8. doi: 10.1097/GCO.0b013e328302143c.
Seppänen-Laakso et al., How to study lipidomes. J Mol Endocrinol. Mar. 2009;42(3):185-90. Epub Dec. 5, 2008.
Sergio et al., Prophylaxis of recurrent preeclampsia: low-molecular-weight heparin plus low-dose aspirin versus low-dose aspirin alone. Hypertens Pregnancy. 2006;25(2):115-27.
Shao et al., Crystallographic analysis of calcium-dependent heparin binding to annexin A2. J Biol Chem. Oct. 20, 2006;281(42):31689-95. Author manuscript.
Sharkey et al., Novel antiangiogenic agents for use in contraception. Contraception. Apr. 2005;71(4):263-71.
Shedden et al., Accurate Molecular Classification of Human Cancers Based on Gene Expression Using a Simple Classifier with a Pathological Tree-Based Framework. Am J Pathol. Nov. 2003;163(5):1985-95.
Sher et al., Effect of vaginal sildenafil on the outcome of in vitro fertilization (IVF) after multiple IVF failures attributed to poor endometrial development. Fertil Steril. Nov. 2002;78(5):1073-6.
Shi et al., Acceleration of skeletal muscle regeneration in a rat skeletal muscle injury model by local injection of human peripheral blood-derived CD133-positive cells. Stem Cells. Apr. 2009;27(4):949-60. doi: 10.1002/stem.4.
Shmelkov et al., AC133/CD133/Prominin-1. Int J Biochem Cell Biol. Apr. 2005;37(4):715-9.
Shoupe et al., Correlation of endometrial maturation with four methods of estimating day of ovulation. Obstet Gynecol. Jan. 1989;73(1):88-92.
Simón et al., Coculture of human embryos with autologous human endometrial epithelial cells in patients with implantation failure. J Clin Endocrinol Metab. Aug. 1999;84(8):2638-46.
Simon et al., Similar endometrial development in oocyte donors treated with either high- or standard-dose GnRH antagonist compared to treatment with a GnRH agonist or in natural cycles. Hum Reprod. Dec. 2005;20(12):3318-27. Epub Aug. 5, 2005.
Singh et al., Autologous stem cell transplantation in refractory Asherman's syndrome: A novel cell based therapy. J Hum Reprod Sci. Apr. 2014;7(2):93-8. doi: 10.4103/0974-1208.138864.
Singh et al., Levels of Prostaglandin F-2-Alpha and Prostaglandin E-2 in human endometrium during the menstrual cycle. Am. J. Obstet. Gynecol. Apr. 21, 1975;121(7):1003-1007.
Sobel, Fibrinolysis and activators of plasminogen. Heart Lung. Nov. 1987;16(6 Pt 2):775-9. Abstract Only.
Steegers et al., Pre-eclampsia. Lancet. Aug. 21, 2010;376(9741):631-44. doi: 10.1016/S01406736(10)60279-6. Abstract Only.
Strowitzki et al., The human endometrium as a fertility-determining factor. Hum Reprod Update. Sep.-Oct. 2006;12(5):617-30. Epub Jul. 10, 2006.
Sucak et al., Increased global fibrinolytic capacity as a clue for activated fibrinolysis in preeclampsia. Blood Coagul Fibrinolysis. Jul. 2006;17(5):347-52. Abstract Only.
Surrenti et al., High performance liquid chromatographic method for prostaglandin E2 determination in human gastric juice without derivatization. J Liquid Chromatography and Rel Technol. Oct. 1984;7(12):2409-19.
Tabanelli et al., In vitro decidualization of human endometrial stromal cells. J Steroid Biochem Mol Biol. May 1992;42(3-4):337-44. Abstract Only.

Tackels-Horne et al., Identification of differentially expressed genes in hepatocellular carcinoma and metastatic liver tumors by oligonucleotide expression profiling. Cancer. Jul. 15, 2001;92(2):395-405.
Talbi et al., Molecular Phenotyping of Human Endometrium Distinguishes Menstrual Cycle Phases and Underlying Biological Processes in Normo-Ovulatory Women. Endocrinology. Mar. 2006;147(3):1097-121. Epub Nov. 23, 2005.
Tapia et al., Differences in the endometrial transcript profile during the receptive period between women who were refractory to implantation and those who achieved pregnancy. Hum Reprod. Feb. 2008;23(2):340-51. Epub Dec. 12, 2007.
Taylor, Endometrial cells derived from donor stem cells in bone marrow transplant recipients. JAMA. Jul. 7, 2004;292(1):81-5.
Thomas et al., Endometrial integrin expression in women undergoing in vitro fertilization and the association with subsequent treatment outcome. Fertil Steril. Sep. 2003;80(3):502-7.
Tsang et al., Prostaglandin secretion by human endometrium in vitro. American Journal of Obstetrics and Gynecology. 1982;142(6):626-633. Abstract only.
Tsapanos et al., The role of Seprafilm bioresorbable membrane in the prevention and therapy of endometrial synechiae. J Biomed Mater Res. 2002;63(1):10-4.
Uchida et al., Direct isolation of human central nervous system stem cells. Proc Natl Acad Sci U S A. Dec. 19, 2000;97(26):14720-5.
Urbich et al., Endothelial progenitor cells: characterization and role in vascular biology. Circ Res. Aug. 20, 2004;95(4):343-53.
Van Der Gaast et al., Endometrial secretion aspiration prior to embryo transfer does not reduce implantation rates. Reprod Biomed Online. Jul.-Aug. 2003;7(1):105-9.
Van Der Gaast et al., the feasibility of a less invasive method to assess endometrial maturation—comparison of simultaneously obtained uterine secretion and tissue biopsy. BJOG. Jan. 2009;116(2):304-12.
Vaquerizas et al., GEPAS, an experiment-oriented pipeline for the analysis of microarray gene expression data. Nucleic Acids Res. Jul. 1, 2005;33(Web Server issue):W616-20.
Ventolini et al., Hysteroscopy in the evaluation of patients with recurrent pregnancy loss: a cohort study in a primary care population. Surg Endosc. Dec. 2004;18(12):1782-4. Epub Oct. 26, 2004.
Vinnars et al., The severity of clinical manifestations in preeclampsia correlates with the amount of placental infarction. Acta Obstet Gynecol Scand. Jan. 2011;90(1):19-25. doi:10.1111/j.1600-0412.2010.01012.x. Abstract Only.
Voyksner et al., Determination of prostaglandins, and other metabolites of arachidonic acid by thermospray HPLC/MS using post column derivatization. Biomed Environ Mass Spectrom. May 1987;14(5):213-20.
Wang et al., Roadmap to embryo implantation: clues from mouse models. Nat Rev Genet. Mar. 2006;7(3):185-99.
Wasielak et al., Effect of the conceptus on uterine prostaglandin-F2alpha and prostaglandin-E2 release and synthesis during the periimplantation period in the pig. Reprod Fertil Dev. 2009;21(5):709-17.
Wilcox et al., Time of implantation of the conceptus and loss of pregnancy. N Engl J Med. Jun. 10, 1999;340(23):1796-9.
Woclawek-Potocka et al., Phytoestrogen metabolites are much more active than phytoestrogens themselves in increasing prostaglandin F(2alpha) synthesis via prostaglanin F(2alpha) synthase-like 2 stimulation in bovine endometrium. Prostaglandins Other Lipid Mediat. Dec. 2005;78(1-4):202-17. Epub Oct. 27, 2005.
Wolff et al., Demonstration of multipotent stem cells in the adult human endometrium by in vitro chondrogenesis. Reprod Sci. Sep. 2007;14(6):524-33.
Xin et al., Alterations of profibrinolytic receptor annexin A2 in pre-eclampsia: a possible role in placental thrombin formation. Thromb Res. May 2012;129(5):563-7. doi: 10.1016/j.thromres.2011.07.039. Epub Aug. 24, 2011.
Zhang et al., Transcatheter Arterial Infusion of Autologous CD133+ Cells for Diabetic Peripheral Artery Disease. Stem Cells Int. 2016;2016:6925357. doi: 10.1155/2016/6925357. Epub Feb. 14, 2016.

(56) References Cited

OTHER PUBLICATIONS

Zhao et al., Uterine infusion with bone marrow mesenchymal stem cells improves endometrium thickness in a rat model of thin endometrium. Reprod Sci. Feb. 2015;22(2):181-8. doi: 10.1177/1933719114537715. Epub Jun. 19, 2014.

Zhou et al., Cigarette smoke inhibits recruitment of bone-marrow-derived stem cells to the uterus. Reprod Toxicol. Feb. 2011;31(2):123-7. doi: 10.1016/j.reprotox.2010.10.007. Epub Oct. 15, 2010. Author manuscript.

Zhou et al., Preeclampsia is associated with abnormal expression of adhesion molecules by invasive cytotrophoblasts. J Clin Invest. Mar. 1993;91(3):950-60.

Zhou et al., Preeclampsia is associated with failure of human cytotrophoblasts to mimic a vascular adhesion phenotype. One cause of defective endovascular invasion in this syndrome? J Clin Invest. May 1, 1997;99(9):2152-64.

Zhou et al., Reversal of gene dysregulation in cultured cytotrophoblasts reveals possible causes of preeclampsia. J Clin Invest. Jul. 2013;123(7):2862-72. doi: 10.1172/JCI66966. Erratum in: J Clin Invest. Oct. 1, 2013;123(10):4541.

Extended European Search Report dated Aug. 12, 2019 in connection with Application No. EP 19169309.2.

Santamaria et al., Uterine stem cells: from basic research to advanced cell therapies. Hum Reprod Update. Nov. 1, 2018;24(6):673-693. doi: 10.1093/humupd/dmy028.

Santamaria et al., Bone Marrow Stem Cell Treatment for Asherman's Syndrome and Endometrial Atrophy. ClinicalTrials. Apr. 21, 2015. <https://clinicaltrials.gov/ct2/history/NCT02144987?A=1&B=5&C=merged#StudyPageTop>. 9 pages. [Accessed May 1, 2020].

\* cited by examiner

FIG. 1
A. STUDY DESIGN
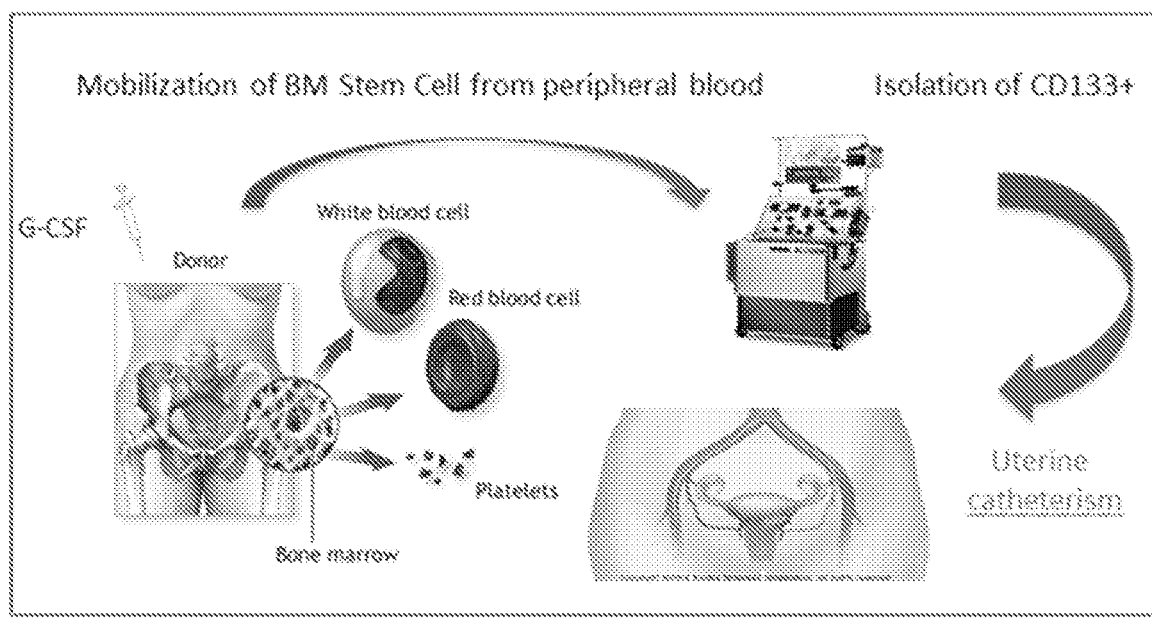
B. Time line
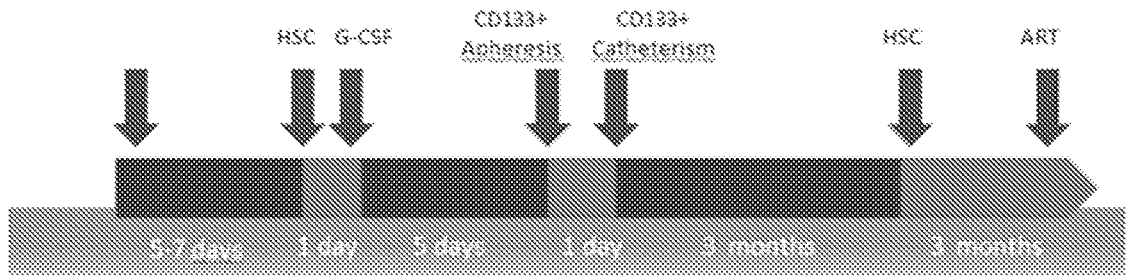

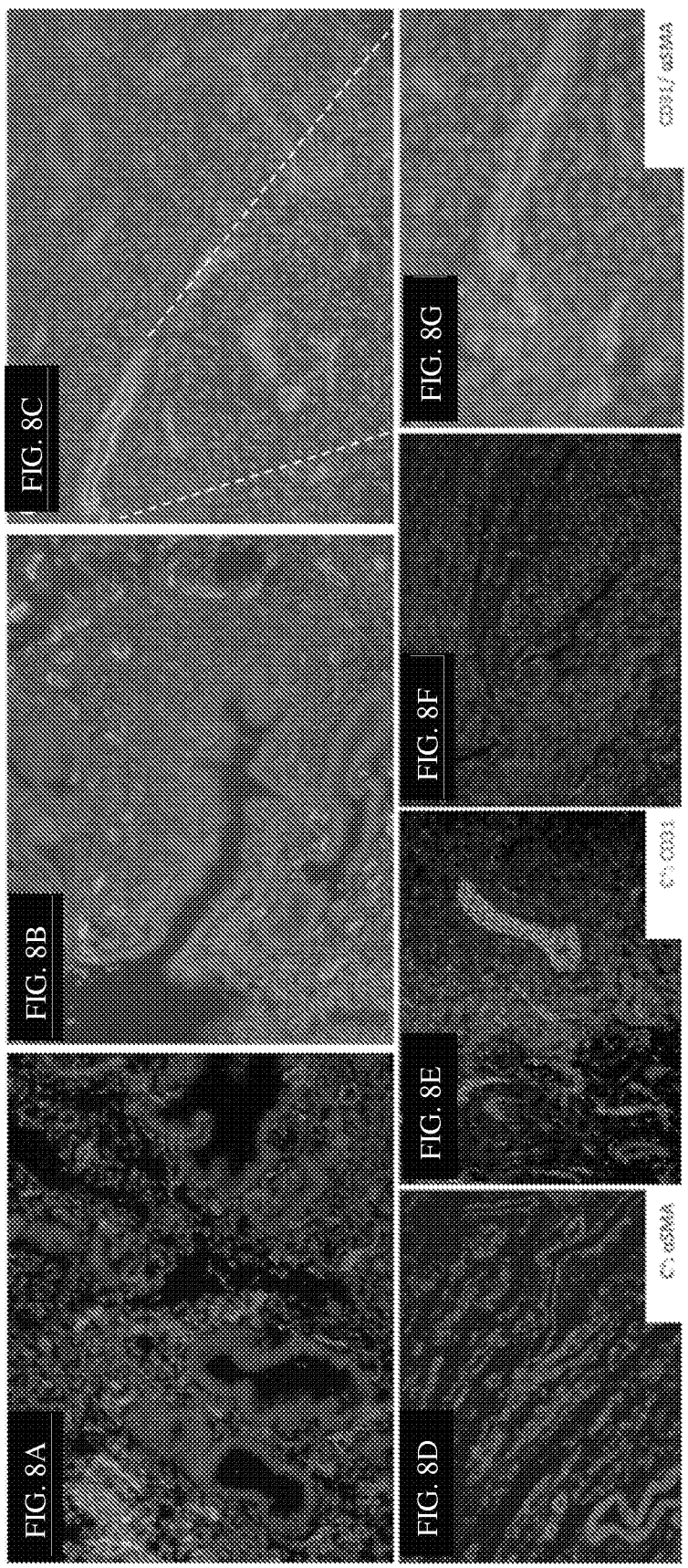

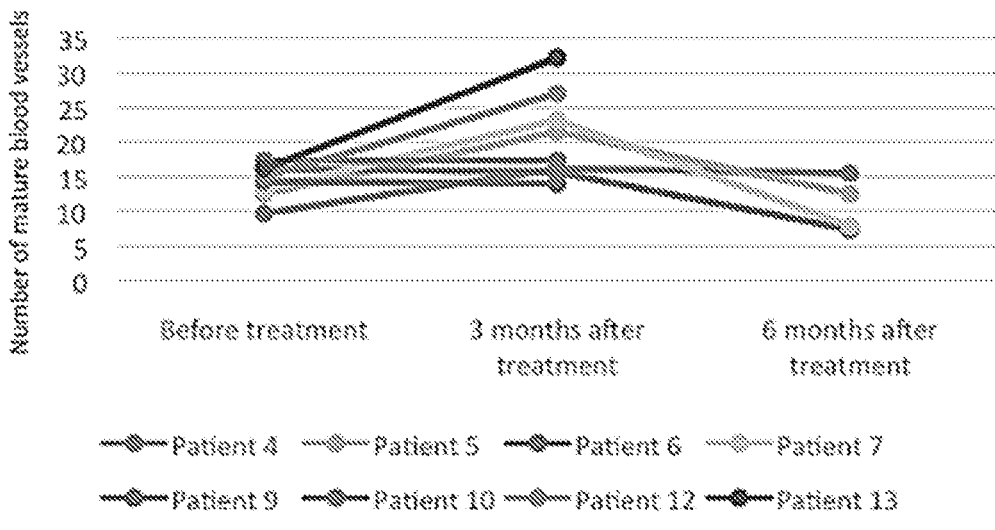
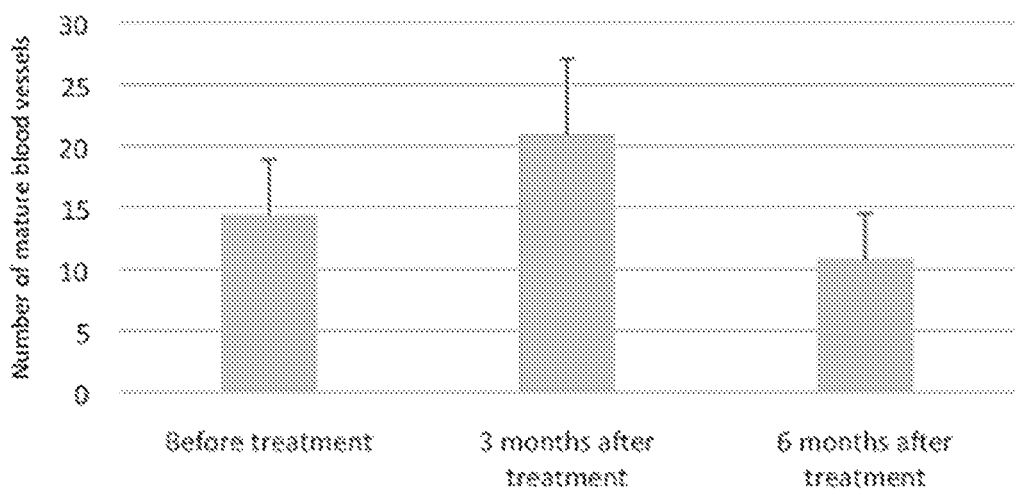

STEM CELL THERAPY IN ENDOMETRIAL PATHOLOGIES

RELATED APPLICATIONS

This application is a national stage filing under 35 U.S.C. § 371 of international application PCT/IB2015/001715, entitled "STEM CELL THERAPY IN ENDOMETRIAL PATHOLOGIES," filed Jun. 5, 2015, which was published under PCT Article 21(2) in English and which claims the benefit under 35 U.S.C. § 119(e) of U.S. Provisional Application No. 62/013,121, filed Jun. 17, 2014, the entire contents of each of which are hereby incorporated by reference.

FIELD OF THE INVENTION

The present invention generally relates to the use of autologous CD133+ bone marrow stem cells (BMDSC) to induce endometrial regeneration and treat endometrial pathologies such as Asherman's syndrome and endometrial atrophy.

BACKGROUND OF THE INVENTION

In a woman of reproductive age, two layers of endometrium can be distinguished: (i) the functional layer adjacent to the uterine cavity, and (ii) the basal layer, adjacent to the myometrium and below the functional layer. The functional layer is built up after the end of menstruation during the first part of the previous menstrual cycle. Proliferation is induced by estrogen (follicular phase of menstrual cycle), and later changes in this layer are produced by progesterone from the corpus luteum (luteal phase). It is adapted to provide an optimum environment for the implantation and growth of the embryo. This layer is completely shed during menstruation. In contrast, the basal layer is not shed at any time during the menstrual cycle. Regeneration of the human endometrium under systemic ovarian steroids changes in each menstrual cycle is essential for the preparation of this organ for its main function, i.e., the development of the endometrial window of implantation to host the implanting blastocyst, allowing pregnancy to occur. Thus, replenishment of all cellular compartments of the endometrial functionalis layer with each menstrual cycle is essential for normal reproductive function.

Asherman's Syndrome (AS) is a condition in which there is a destruction of the endometrium caused by repeated or aggressive curettages and/or endometritis. It produces an obliteration of the uterine cavity with intrauterine adhesions and absence of functional endometrium in many areas. Women with this disease as well with atrophic endometrium (<4 mm) often struggle with infertility, menstrual irregularities including amenorrhea, hypomenorrhea, and recurrent pregnancy losses. Currently no specific treatment for these endometrial pathologies exist. Thus, there remains a need to develop safe and effective therapies to treat these pathologies.

SUMMARY OF THE INVENTION

The present disclosure relates, at least in part, to the discovery that autologous CD133+ bone marrow derived stem cells (BMDSC) can regenerate vascularization that leads to the creation of autologous functional endometrium de novo. Accordingly, aspects of the disclosure provide methods to induce endometrial regeneration. In some embodiments, the method comprises administering an effective amount of autologous CD133+ bone marrow derived stem cells (BMDSC) into uterine arteries of a subject in need thereof to induce endometrial regeneration.

In some embodiments, the subject is known to have Asherman's syndrome or endometrial atrophy. In some embodiments, the subject has endometrial atrophy that is resistant to hormonal treatment. In some embodiments, the subject has had one or more prior embryo implantation failures. In some embodiments, the autologous CD133+ BMDSC are prepared by administering to the subject an agent to mobilize BMDSC from bone marrow into peripheral blood of the subject; and isolating CD133+ BMDSC from peripheral blood of the subject. In some embodiments, the agent to mobilize BMDSC is granulocyte colony-stimulating factor (G-CSF). In some embodiments, the autologous CD133+ BMDSC are isolated from peripheral circulation of the subject by apheresis using an anti-CD133 antibody. In some embodiments, the CD133+ BMDSC are administered into the uterine arteries through a catheter. In some embodiments, the CD133+ BMDSC are administered into the uterine spiral arterioles of the subject.

Some aspects of the disclosure provide a method to induce endometrial regeneration, the method comprising isolating autologous CD133+ bone marrow derived stem cells (BMDSC) from a subject in need thereof; and administering an effective amount of the isolated CD133+ BMDSC into the uterine arteries of the subject to induce endometrial regeneration.

In some embodiments, granulocyte colony-stimulating factor (G-CSF) is administered to the subject before isolating the autologous BMDSC. In some embodiments, the autologous CD133+ BMDSC are isolated from peripheral circulation of the subject by apheresis using an anti-CD133 antibody. In some embodiments, the CD133+ BMDSC are administered into the uterine arteries through a catheter. In some embodiments, the CD133+ BMDSC are administered into the uterine spiral arterioles of the subject. In some embodiments, the subject is known to have Asherman's syndrome or endometrial atrophy. In some embodiments, the subject has endometrial atrophy that is resistant to hormonal treatment. In some embodiments, the subject has had one or more prior embryo implantation failures.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

FIG. 1 is a schematic showing the study design (A) and time line (B) of the events depicted in FIG. 1A.

FIGS. 8A-8I show tissue analyses. Immunohistochemical results for the detection of mature blood vessels in the endometrium from patient 7 before (FIG. 8A), 3 months (FIG. 8B) and 6 months (FIG. 8C) after autologous cell therapy. α-sma+, CD31+ positive cells identify mature blood vessels (20×). FIG. 8D shows human myometrium used as a positive control for α-sma staining, and human tonsil used as a positive control for CD31 (FIG. 8E). FIG. 8F shows the negative control resulting from the absence of primary antibody. FIG. 8G presents a detailed view of the vessel identified in FIG. 8C (40×). In FIG. 8H, the dynamics of the total number of mature blood vessels from 8 patients before, and 3 and 6 months after cell therapy is presented, indicating a time-sensitive neoangiogenic effect. FIG. 8I shows the statistical analysis of the mean±SEM of total mature blood vessels before and 3 and 6 months after treatment.

DETAILED DESCRIPTION OF THE INVENTION

Figure 2:
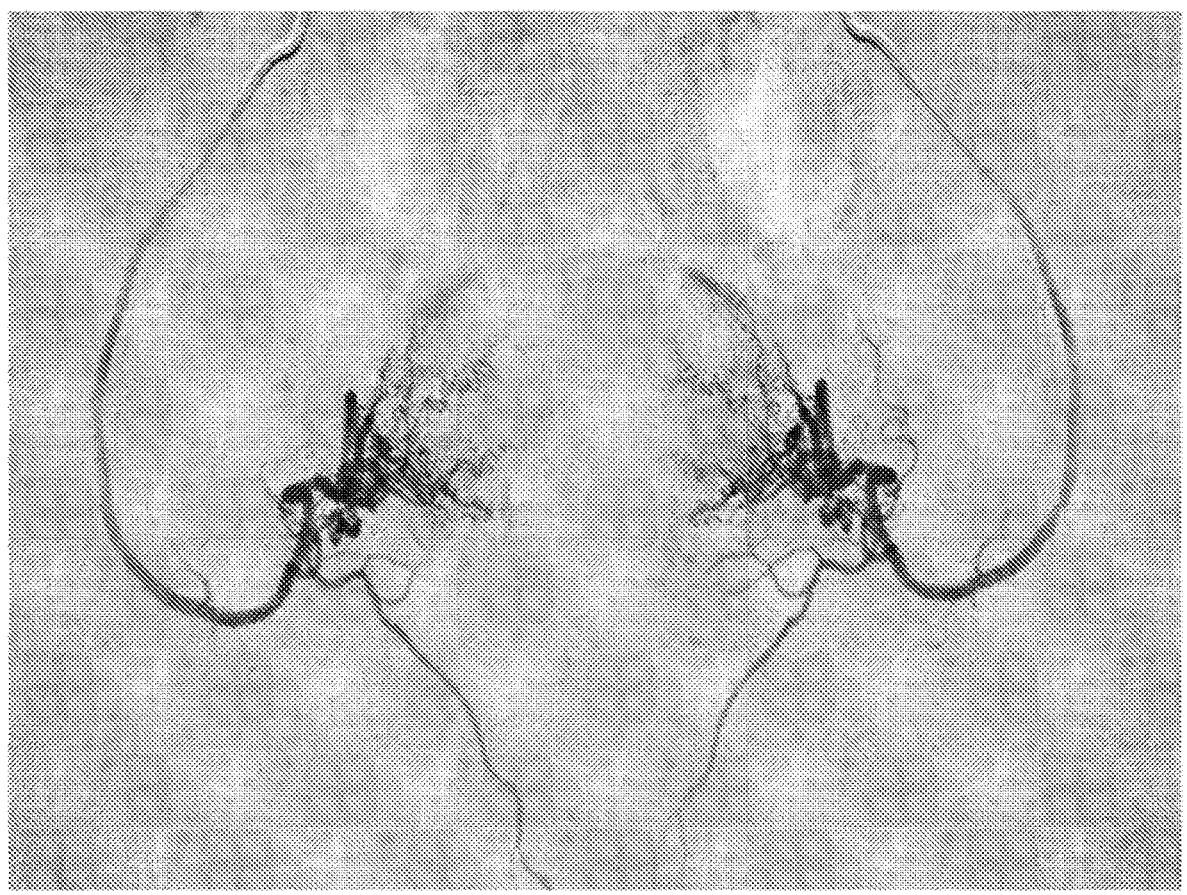
FIG. 2 is an angiography demonstrating the path of the probe from uterine arteries through spiral arterioles where the CD133+ cells are situated through non-invasive radiology.
Figure 3:
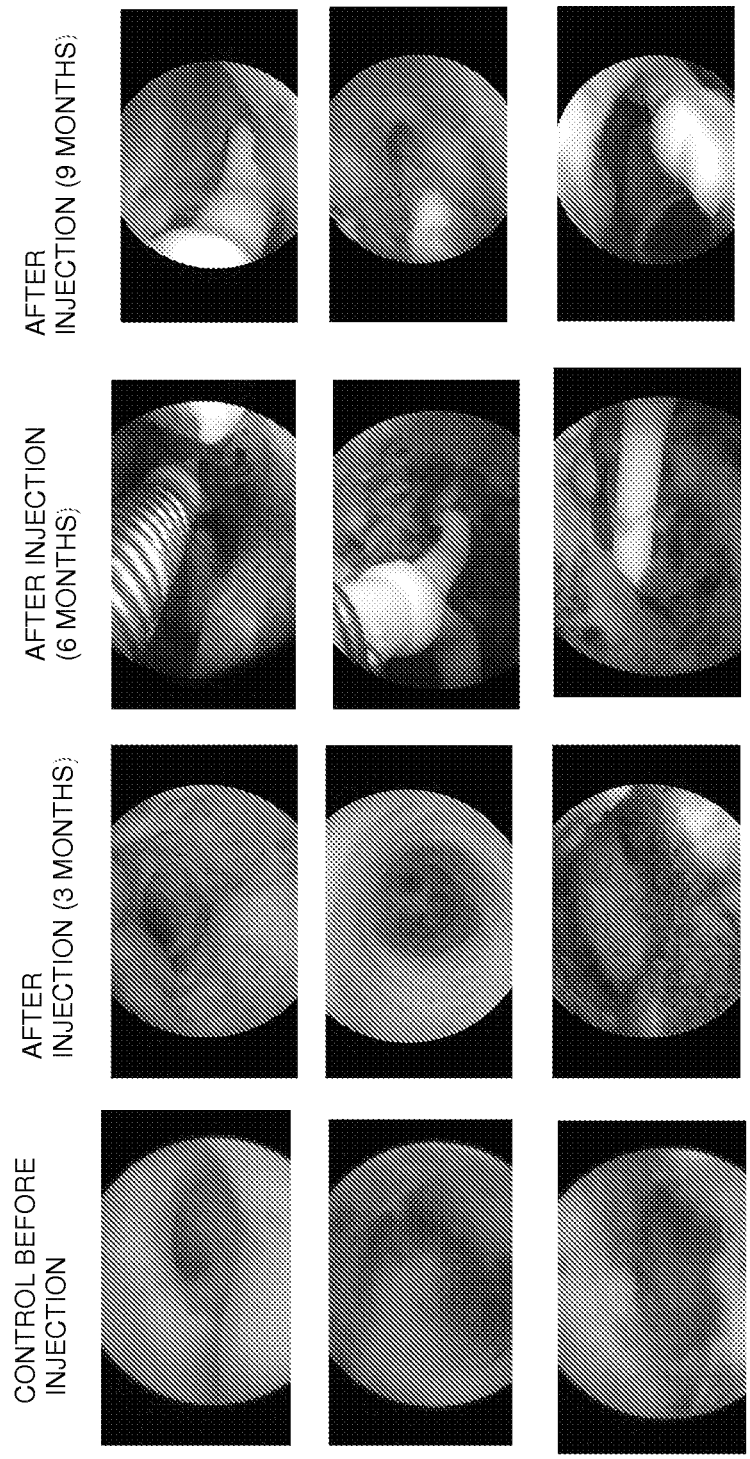
FIG. 3 shows hysteroscopy of the uterine cavity from one patient with atrophic endometrium before, 3-6 and 9 months after the autologous BMSC treatment.
Figure 4:
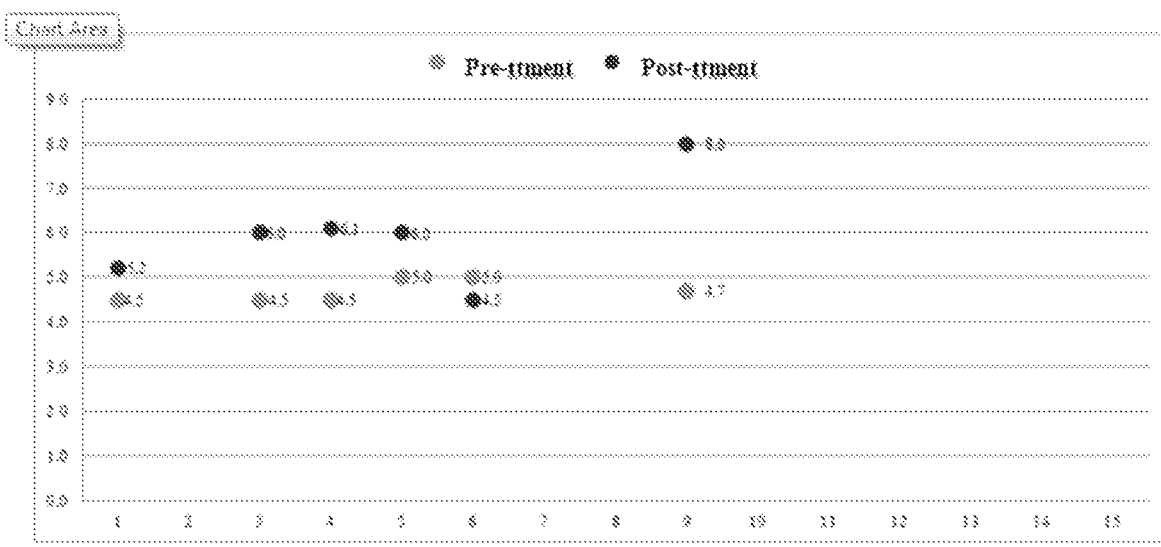
FIG. 4 demonstrates the endometrial thickness in 6 patients with atrophic endometrium/Asherman syndrome included in this study, before and 3 months after autologous BMSC therapy.
Figure 5:
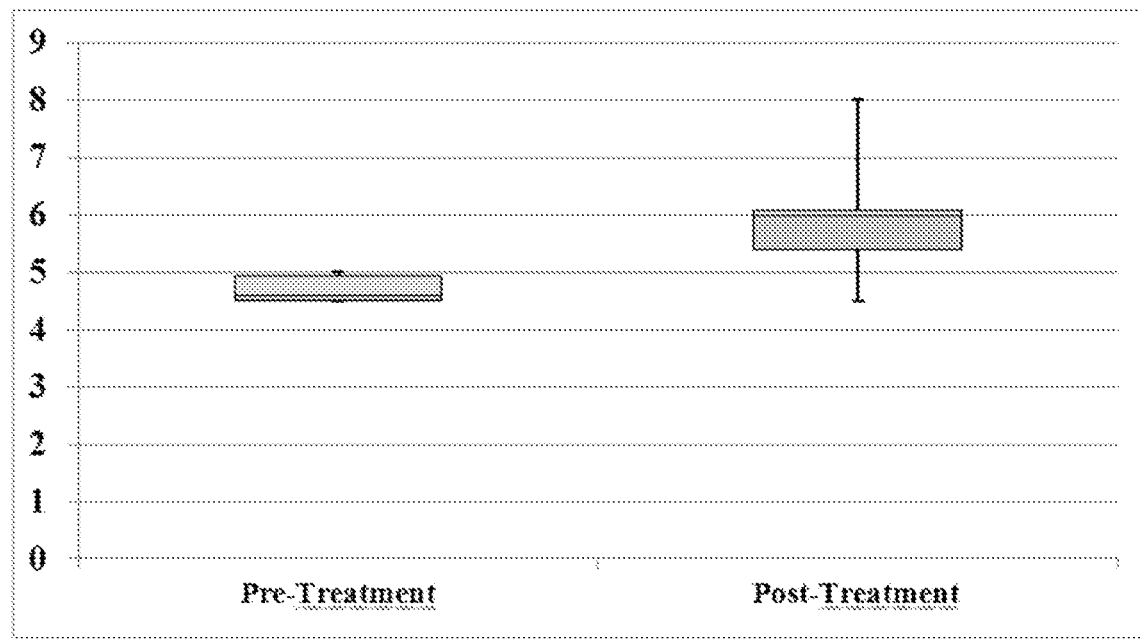
FIG. 5 shows the mean+SD endometrial thickness before and 3 months after autologous BMSC treatment.
Figure 6:
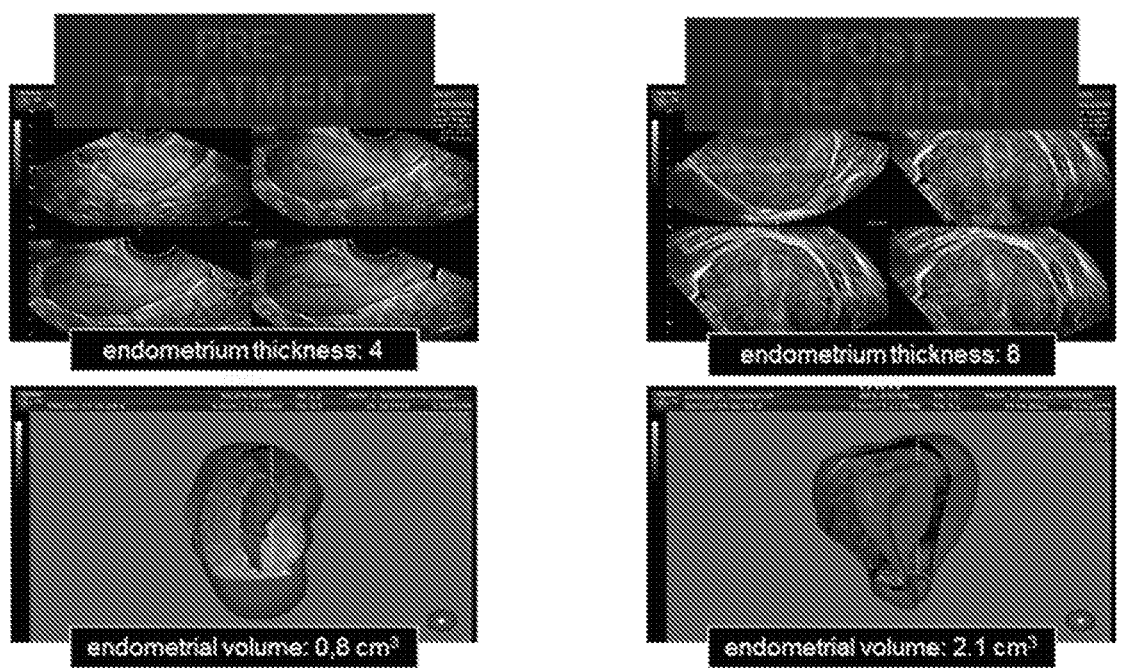
FIG. 6 shows 3D ultrasound images demonstrating the improvement of endometrial volume obtained 3 months after autologous BMSC therapy compared to pretreatment basal status.

The present invention is based, at least in part, on the discovery of a new therapeutic approach to induce endometrial regeneration using autologous stem cell therapy. In particular, the present application is based on the finding that autologous CD133+ bone marrow derived stem cells (BMDSC) can regenerate vascularization that leads to the creation of autologous functional endometrium de novo. Although BMDSCs were known to be a source of non-hematopoietic cells in the different endometrial cellular compartments (stroma, glandular epithelium, and luminal epithelium), it was not known which subpopulation(s) of BMDSCs promote(s) the repair of the endometrium. The present application provides safe and effective cell-based therapies to induce endometrial regeneration and treat pathologies associated with endometrial degeneration such as Asherman's Syndrome and endometrial atrophy.

The human uterus mainly consists of the endometrium and the outer smooth muscle layer termed the myometrium. The functional layer of the human endometrium is a highly regenerative tissue undergoing monthly cycles of growth, differentiation and shedding during a woman's reproductive years. Fluctuating levels of circulating estrogen and progesterone orchestrate this dramatic remodeling of human endometrium. Endometrial regeneration also follows parturition and endometrial resection. Endometrial regeneration from the basal layer contributes to the replacement of the functionalis layer followed by its slough off during menses and parturition. However, the endometrium may fail to respond to estrogen and not regenerate in certain pathologies, for example, Asherman's Syndrome and atrophy of the endometrium. Such subjects may experience abnormal endometrial proliferation and become infertile.

Asherman's syndrome (AS) (or Fritsch syndrome) is a condition characterized by adhesions and/or fibrosis of the endometrium most often associated with dilation and curettage of the intrauterine cavity. A number of other terms have been used to describe the condition and related conditions including: intrauterine adhesions (IUA), uterine/cervical atresia, traumatic uterine atrophy, sclerotic endometrium, endometrial sclerosis, and intrauterine synechiae. Trauma to the endometrial basal layer, for example, after a dilation and curettage (D&C) performed after a miscarriage, or delivery, or for medical abortion, can lead to the development of intrauterine scars resulting in adhesions that can obliterate the uterine cavity to varying degrees. In the extreme, the whole cavity can be scarred and occluded. Even with relatively few scars, the endometrium may fail to respond to estrogen, and a subject may experience secondary menstrual irregularities (such as amenorrhea, hypomenorrhea, or oligomenorrhea) and become infertile. AS can also result from other pelvic surgeries including cesarean sections, removal of fibroid tumors (myomectomy) and from other causes such as IUDs, pelvic irradiation, schistosomiasis and genital tuberculosis. Chronic endometritis from genital tuberculosis is a significant cause of severe intrauterine adhesions (IUA) in the developing world, often resulting in total obliteration of the uterine cavity which is difficult to treat.

Hysteroscopy is the gold standard for diagnosis of AS. Imaging by sonohysterography or hysterosalpingography reveals the extent of the scar formation. Depending on the degree of severity, AS may result in infertility, repeated miscarriages, pain from trapped blood, and future obstetric complications. If left untreated, the obstruction of menstrual flow resulting from adhesions can lead to endometriosis in some cases.

In endometrial atrophy, the endometrium becomes too thin as a result of low estrogen levels. To be considered atrophic, the endometrial thickness should measure less than 4-5 mm on a transvaginal ultrasound scan. The uterine body to cervix ratio will also tend to decrease and may approach 1:1. A MRI can also demonstrate a decrease in endometrial thickness similar to that observed with ultrasound. Factors that can cause endometrial atrophy include prolonged oral contraception, hypo-oestrogenic state (ovarian dysfunction) and Tamoxifen use.

According to one aspect of the invention, a method to induce endometrial regeneration is provided. The method comprises administering an effective amount of autologous CD133+ bone marrow derived stem cells (BMDSC) into uterine arteries of a subject in need thereof to induce endometrial regeneration.

According to one aspect of the invention, a method to induce endometrial regeneration is provided. The method comprises isolating autologous CD133+ bone marrow derived stem cells (BMDSC) from a subject in need thereof; and administering an effective amount of the isolated CD133+ BMDSC into the uterine arteries of the subject to induce endometrial regeneration.

As used herein, "a subject" includes all mammals, including, but not limited to, dogs, cats, horses, sheep, goats, cows, pigs, humans, and non-human primates. In some embodiments, the subject is a woman.

A subject in need of endometrial regeneration is a subject whose endometrium fails to regenerate in response to estrogen and has a thin endometrial lining. Such subjects often experience abnormal endometrial proliferation and become infertile. The optimal thickness for the endometrial lining is between 10 and 15 mm, reaching its maximum thickness at the time of implantation at around day 21 of a woman's menstrual cycle. In some embodiments, the subject in need of treatment has an endometrial thickness at the time of implantation that is less than 5 mm, less than 4 mm, less than 3 mm, less than 2 mm or less than 1 mm. In some embodiments, the subject has menstrual irregularities characterized by a decrease in flow and duration of bleeding (amenorrhea, hypomenorrhea, or oligomenorrhea) and/or recurrent pregnancy losses. In some embodiments, the subject is known to have Asherman's Syndrome or endometrial atrophy. In some embodiments, the subject has endometrial atrophy that is resistant to hormonal treatment. In some embodiments, the subject has had one or more prior embryo implantation failures.

Bone marrow-derived stem cells (BMDSCs) have been shown to contribute as an exogenous source to tissue repair and regeneration of different organs and tissues. In the human and murine endometrium, BMDSCs are also a source of non-hematopoietic cells in the different endometrial cellular compartments (stroma, glandular epithelium, and luminal epithelium). They contribute mainly to the formation of endometrial stromal compartment cells and to a much lesser extent to the endometrial glandular and luminal epithelial compartments.

BMDSCs include hematopoietic stem cells (HSCs), and mesenchymal stem cells (MSCs). However, which subpopulation(s) of BMDSCs promote(s) the repair of the endometrium was unknown.

The inventors of the present application have demonstrated for the first time in humans the ability of CD133$^+$ bone marrow derived stem cells delivered into uterine arteries via surgical and catheter delivery systems to induce endometrial regeneration. Autologous circulating CD133$^+$ BMDSC were isolated after previous bone-marrow mobilization and re-implanted into the spiral arterioles of the uterus of the same patient. The CD133$^+$ BMDSC regenerate vascularization that leads to the creation of an autologous functional endometrium de novo. CD133 is a glycoprotein also known in humans and rodents as Prominin 1 (PROM1). It is a five-transmembrane-spanning cholesterol binding protein that localizes to membrane protrusions and is often expressed on adult stem cells, where it is thought to function in maintaining stem cell properties by suppressing differentiation.

The CD133$^+$ BMDSC of the present invention may be derived from primary stem cells or may be derived from an established stem cell line. In some embodiments, stem cells may be embryonic stem cells, adult stem cells, umbilical cord blood stem cells, somatic stem cells, bone marrow or mobilized bone marrow stem cells. In preferred embodiments, the stem cells are adult stem cells.

In some embodiments, the CD133$^+$ BMDSC are prepared by administering to the subject an agent to mobilize BMDSC from bone marrow into peripheral blood of the subject; isolating CD133$^+$BMDSC from peripheral blood of the subject. In some embodiments, the stem cell mobilizing agent is selected from the group consisting of granulocyte colony-stimulating factor (G-CSF), granulocyte macrophage-colony stimulating factor (GM-CSF), and plerixafor (AMD3100). In some embodiments, the stem cell mobilizing agent is G-CSF.

In some embodiments, the autologous CD133$^+$ BMDSC are isolated from peripheral circulation of the subject by a process called apheresis using an anti-CD133 antibody (see, for example, Sovalat H, Scrofani M, Eidenschenk A, Pasquet S, Rimelen V, Hénon P. Identification and isolation from either adult human bone marrow or G-CSF-mobilized peripheral blood of CD34(+)/CD133(+)/CXCR4(+)/Lin(−)CD45(−) cells, featuring morphological, molecular, and phenotypic characteristics of very small embryonic-like (VSEL) stem cells. Exp Hematol. 2011 April; 39(4):495-505, the entire contents of which are incorporated herein in their entirety). Apheresis, which is a well-known process in the art, refers to the process or procedure in which blood is drawn from a donor subject and separated into its components, some of which are retained, such as stem cell populations, and the remainder returned by transfusion to the donor subject. Apheresis takes longer than a whole blood donation. A whole blood donation takes about 10-20 minutes to collect the blood, while an apheresis donation may take about 1-2 hours. The apheresis product refers to the heterogeneous population of cells collected from the process of apheresis.

In some embodiments, the CD133$^+$ BMDSC are isolated from the isolated BMDSC using an anti-CD133 antibody. In some embodiments, the CD133$^+$ BMDSC are selected using an anti-CD133 antibody until the CD133$^+$ BMDSC are at least 80%, 85%, 90%, 95%, 98%, 99%, 99.9% or 100% pure. In some embodiments, the CD133$^+$ BMDSC are at least 95%, 98%, 99%, 99.9% or 100% pure.

Administration of CD133$^+$ BMDSC, or therapeutic compositions comprising such cells, to subject in need thereof, can be accomplished, e.g., by transplantation, implantation (e.g., of the cells themselves or the cells as part of a matrix-cell combination), injection (e.g., directly into uterine arteries), infusion, delivery via catheter, or any other means known in the art for providing cell therapy. In one embodiment, the cells are delivered by intra-arterial catheterization. The catheterization procedure of the uterine artery has been widely described and used in the embolization of uterine myomas (Ravina J H, Herbreteau D, Ciraru-Vigneron N, et al. Arterial embolisation to treat uterine myomata. Lancet 1995; 346(8976):671-2, the entire contents of which are incorporated herein in their entirety).

The CD133$^+$ BMDSC can be administered into the uterine arteries of the subject. These arteries supply blood to the uterus. In some embodiments, the CD133+ BMDSC are administered into the uterine spiral arterioles of the subject. Spiral arteries are small arteries which temporarily supply blood to endometrium of the uterus during the luteal phase of the menstrual cycle. These arteries are highly sensitive to the estrogens and progesterone, penetrate the endometrial functional layer, grow and send branches within it and exhibit very different and unique patterns.

The CD133$^+$ BMDSC are administered in an effective amount. An "effective amount" refers to an amount sufficient to elicit the desired biological response, i.e., inducing endometrial regeneration. An effective amount includes that amount necessary to slow, reduce, inhibit, ameliorate or reverse one or more symptoms associated with AS or endometrial atrophy. In some embodiments, such terms refer to:

- A restart of menstruation after the CD133$^+$BMSC stem-cell treatment;
- An increase of the endometrial thickness; (Endometrial thickness is measured as the length from the superior to inferior myometrial limit in the fundus of the endometrial cavity. For example, the increase can be an increase of 50% of the maximal thickness ever obtained with hormone replacement therapy (HRT) measured by vaginal ultrasound longitudinal axis at the uterine fundus (vgr from 4 to 6 mm);
- Hysteroscopic and Histological evidences of de novo endometrium formation; and/or
- Functionality of the reconstructed endometrium in terms of live-birth rate, pregnancy and implantation rates after embryo placement in these patients.

In some embodiments, at least 45 million CD133$^+$ BMDSC are instilled into the subject. In some embodiments, at least 50, 55, 60, 65 million CD133$^+$ BMDSC are instilled into the subject.

An effective amount can be determined by one of skill in the art using routine methods. In some embodiments, an effective amount is an amount which results in any improvement in the condition being treated. One of skill in the art can determine appropriate doses and ranges of therapeutic agents to use, for example based on in vitro and/or in vivo testing and/or other knowledge of compound dosages. When administered to a subject, effective amounts of the therapeutic agent will depend, of course, on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1

Materials and Methods
Design

The following is an experimental non-controlled study in 16 patients with refractory AS approved by the IRB of Hospital Clinico de Valencia, Spain and funded by the Spanish Ministry of Health (Ref EC 11-299). BMDSC mobilization was performed using granulocyte-CSF (G-CSF) (5 mg/kg/12 h sc during 4 days). Seven days later, peripheral blood apheresis with isolation of CD133+ cells was performed. Then, autologous CD133+ cells were delivered into the spiral arterioles by a non-invasive radiology intervention through the uterine artery using a 2.5 F microcatheter. Endometrial cavity status was assessed through hysteroscopy, vaginal ultrasound, and histology before, and 3, 6, and 9 months after the stem cell intervention.

Patients & Methods
Inclusion Criteria

Sixteen patients diagnosed with refractory Asherman's syndrome previously treated with surgery at least seven times or with endometrial atrophy (<4 mm) resistant to hormonal treatment with recurrent implantation failure were included in the study. All patients were referred by their respective doctors world-wide to enter the clinical experimental study supported by the Spanish Ministry of Health. Patients' ages ranged from 20-45 years-old, and all had normal liver, heart, and kidney function. The absence of menstrual bleeding in a natural cycle or after hormonal replacement therapy (HRT) was confirmed. The absence of psychiatric pathology, HIV, Hepatitis B or C, and syphilis, as well as a willingness to participate in the study were also confirmed.

Exclusion Criteria

Patients were excluded from the study if there was no access to the peripheral veins or if they had splenomegaly.

Methodology

1. Bone Marrow Stem Cell (BMSC) Mobilization

In order to start the mobilization procedure, the following conditions were met:

- The patient was informed about the procedure and was given the consent form at least 24 hours before the mobilization.
- The corresponding medical evaluation was performed, with the relevant complementary explorations and was validated by the medical doctor responsible for the BMSC recollection.
- The relevant serological test results (HIV, HBcAg, HBsAg, HCV, syphilis) were made available.
- Veins were evaluated to determine their suitability for the procedure.

Then, BMSC mobilization to the peripheral blood was induced by G-CSF (5 mcg/kg sc every 12 hours) for 4 days.

2. BMSC Recollection

The BMSC recollection was done by a conventional apheresis procedure using a peripheral vein. A positive selection of the CD133$^+$ cells was performed following the PO-7610-02 protocol approved by the Hospital Clínico Universitario with the application of three washings and subsequent selection of CD133$^+$ cells. First, the cells were washed and incubated with a monoclonal antibody, then they were washed two additional times, and finally underwent CD133$^+$ selection.

The selection procedure was performed for a maximum of 3 hours or until at least 50 million CD 133$^+$ cells were collected.

3. CD133+ Cells Transplantation into the Uterine Spiral Arterioles by Intra-Arterial Catheterization Twenty-four hours after their isolation, autologous CD133$^+$ cells were diluted in 15-30 cc of saline solution and then instilled into the spiral arteries. Cells were collected through a sterile syringe into a container and brought to the Radiology Department prior to their instillation. At least 45 million cells were instilled.

The catheterization procedure of the uterine artery has been widely described and used in the embolization of uterine myomas. The required radiology equipment for this procedure was a radiosurgical C-arm or an angiography room with an ultrasound scan. Briefly, after gaining access to the common femoral artery using the Seldinger technique, a 4 F catheter was placed into the artery and used to catheterize both hypogastric arteries using an angiographic catheter with a cobra curve 2 and a Terumo guide 0.035 in. A microcatheter 2.5 F was placed with a guide 0.014 in through the cobra catheter and the uterine artery is catheterized until the ascandant curve or until the microcatheter has reached its most distal level. Once the catheter was stabilized and its position had been checked, the CD133+ BMSC were instilled in a saline solution suspension. The diameter of the catheter for the cell injection was 500-600 microns and 15 cc were perfused.

After the intervention, the patient stayed overnight at the hospital and was discharged the next day without complications.

Responsiveness Criteria

This technique is aimed to repopulate the endometrial vascular niche in patients suffering from Asherman's syndrome or endometrial atrophy using CD133$^+$ BMSC in order to reconstruct a functional endometrium capable of allowing embryo implantation in patients undergoing ART with recurrent implantation failure due to the endometrium. Therefore, the following indicators were considered for successful treatment:

- Menstruation outcome, menstruation must restart after the CD133$^+$BMSC treatment.
- The increase of the endometrial thickness. Minimum 50% of the maximal thickness ever obtained with HRT measured by vaginal ultrasound longitudinal axis at the uterine fundus (vgr from 4 to 6 mm)
- Hysteroscopic and Histological evidences of de novo endometrium formed
- Functionality of the reconstructed endometrium in terms of live-birth rate, pregnancy and implantation rates after embryo replacement in these patients Results This is the first case series study using this specific stem cell treatment applied intravascularaly in AS. The incidence of AS varies between 2-22% of infertile women.

G-CSF is the most commonly used cytokine for BMSC mobilization both in autologous and allogeneic donors. This product is generally well-tolerated. However, administering a dose higher than 5 mcg/kg/day has been shown to bring osteomuscular pain in more than 50% of the cases. If this occurs, paracetamol should be administered as an analgesic (500 mg/8 hours), while maintaining the administration of G-CSF. Other less frequently observed complications are: nausea and vomiting, migraine, and insomnia. In each case, a symptomatic treatment should be administered. In general, the symptoms disappear in 3-4 days after stopping the administration of G-CSF, although a feeling of asthenia could last up to 2 weeks from the last dose. Finally, splenic rupture in healthy donors has been associated with the administration of G-SCF. Due to this fact, an abdominal scan should be performed in all patients that present with pain in the left hypochondrium. The splenomegaly detected in those cases should be followed by the immediate suspension of the G-CSF. High levels of alkaline phosphatase and LDH without any related symptoms are often detected. Leucocytosis is quite common, and values are normally less than $70\times10^9$/L.

Example 2

Study Participants

Sixteen patients (ranging from 30-45 years of age) diagnosed either with refractory Asherman's syndrome (AS) based on the American Fertility Society classification (N=11) or endometrial atrophy (N=5) were invited to par-

TABLE 1

Clinical outcome after CD133+ stem cell treatment

|  | Age | Pathology | Number CD133 (mill)/Kg | ART | Results |
|---|---|---|---|---|---|
| Patient 1 | 40 | Asherman Syndrome | 93.5 | Frozen embryo transfer Ovumdonation D3 TET | Cancelled hydrometra |
| Patient 2 | 31 | Asherman S. | 113.02 | ICSI PGD |  |
| Patient 3 | 44 | Asherman S. + Atrophy | 63.44 | 1$^{st}$ Fresh embryo transfer Ovumdonation (DET) Blasto | Pregnancy test: negative |
| Patient 4 | 38 | Asherman S. + Atrophy | 179.4 | 1$^{st}$ Fresh embryo transfer Ovumdonation (DET) Blasto | Pregnancy test: negative |
| Patient 5 | 43 | Atrophy | 42 | Frozen embryo transfer Ovumdonation (DET) Blasto | Cancelled: irregular endometrium |
| Patient 6 | 45 | Asherman S. | 122.8 | Frozen embryo transfer Ovumdonation (DET) Blasto | Cancelled: thin and irregular endometrium |
| Patient 7 | 34 | Atrophy | 200 | ICSI PGD |  |
| Patient 8 | 35 | Atrophy | 113 | Frozen embryo transfer PGD |  |
| Patient 9 | 41 | Asherman S. + Atrophy | 184.7 | Frozen embryo transfer (DET) D3 // Frozen embryo transfer (DET) D5 | Pregnancy test: negative |

TABLE 2

Cycle length, and menstruation quantity and duration in days after CD133+ BMDCC autologous transplantation

| Menstruation | Regularity (days) | Quantity (Number protections/day) | Duration (days) |
|---|---|---|---|
| 2$^{nd}$ Month post-treatment | 26.5 | 2.6 | 3.8 |
| 4$^{th}$ Month post-treatment | 25.4 | 1.6 | 3.1 |
| 6$^{th}$ Month post-treatment | 26.1 | 1.4 | 2.1 | ticipate in the study. The earlier diagnosis of severe Asherman's syndrome or endometrial atrophy was confirmed, and hysteroscopies were performed in the proliferative phase. Patients diagnosed with AS were classified according to AFS Classification of Uterine Adhesions, and endometrial biopsies were obtained. All patients experienced little or no menstrual bleeding during their natural cycles or after hormonal replacement therapy (HRT). Requirements for participation in the study included the following: normal liver, heart, and kidney function, the absence of HIV, Hepatitis B or C, syphilis, and psychiatric pathology, and a willingness to complete the study. Patients were excluded in instances where there was no peripheral vein access or splenomegaly.

BMDSCs Mobilization and Isolation

Mobilization of BMDSCs was induced by a pharmacological administration of granulocyte colony stimulating factor (G-CSF) (10 ug/kg/day on days −4, −3, −2 and −1). G-CSF is a cytokine extensively used for this purpose in both autologous and allogeneic donors. Five days after the injection, isolation of CD133+ cells were isolated through apheresis via peripheral veins using the CobeSpectra separator (Terumo BCT, Lakewood, Colo.). Two to three samples were processed per patient and a positive selection of CD133+ cells was obtained following an established protocol using the CliniMACS® system (Miltenyi Biotec GmbH, Bergisch Gladbach, Germany). The selection was performed within three hours of the collection until 50 million cells were obtained. Isolated CD133+ cells were diluted into 15 to 30 cc of saline solution and transported in a sterile syringe to the radiology department for delivery into spiral arterioles.

Delivery of BMDSCs

Figure 9:
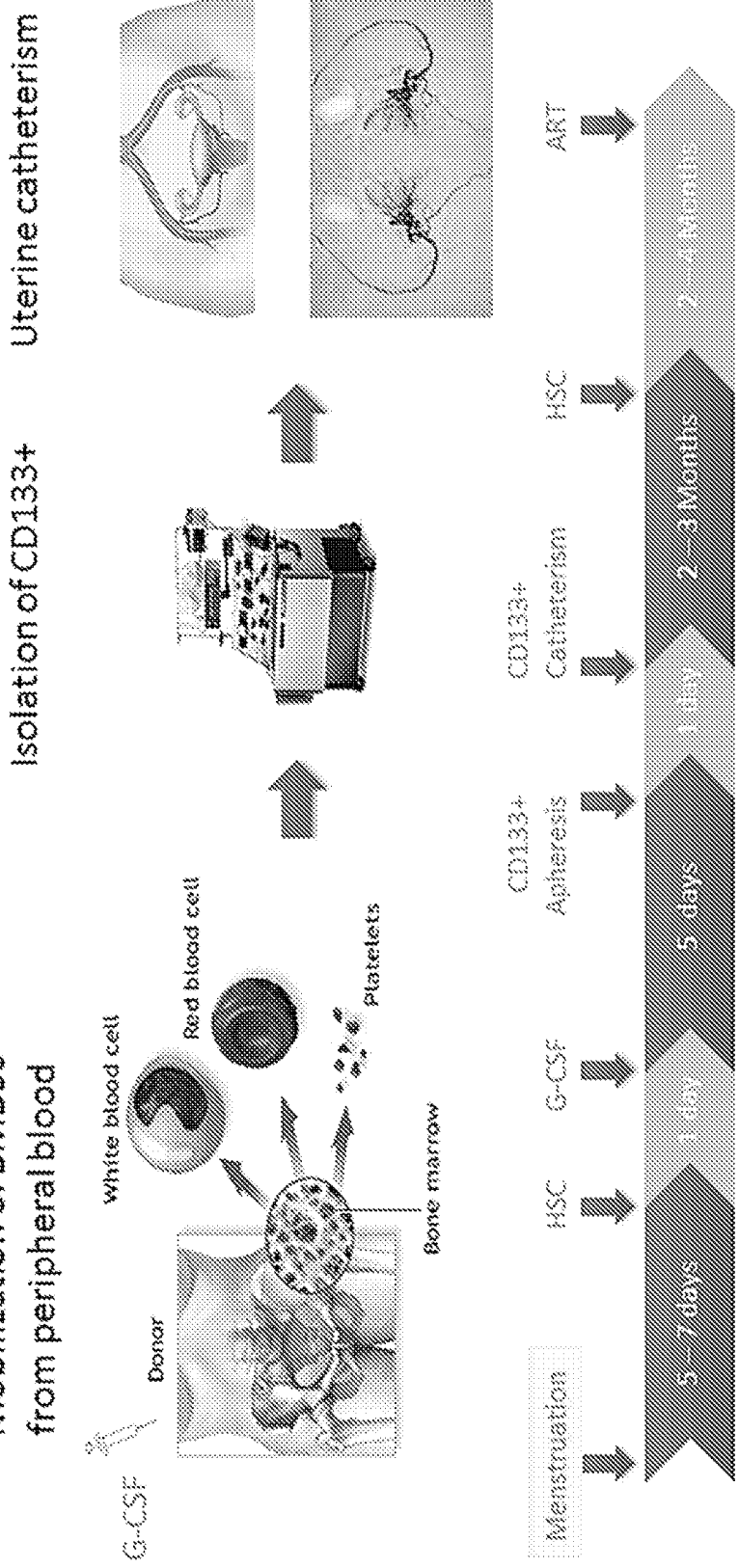
FIG. 9 shows the study design. Hysteroscopic reconfirmation and grading of the AS or EA was performed by one surgeon in the proliferative phase. BMDSC mobilization was induced by G-CSF injection, and five days later, CD133+ cells were isolated from peripheral blood through apheresis and immediately instilled into the spiral arteries by interventional radiology. A second and third look hysteroscopy was conducted to assess the uterine cavity after stem cell treatment. The patients were then invited to attempt to conceive.

After successful CD133+ isolation, patients were referred to the radiology department of HCU, where intra-arterial catheterization was performed to deliver the cells to the endometrial stem cell niche using a technique used for the embolization of fibroids. The common femoral artery was approached using the Seldinger technique, in which a 4 F introducer allowed the catheterization of both hypogastric arteries with an angiographic catheter curve and a guide Terumo (0.035 in). Through the latter catheter, a 2.5 F microcatheter with a guide (0.014 in) was introduced to catheterize the uterine artery to the most distal spiral arterioles the microcatheter could reach (FIG. 9). Once the catheter position was stabilized and verified, 15 cc of a saline suspension of the selected CD133+ cells (containing 42 to $200 \times 10^6$ cells, mean $123.56 \times 10^6 \pm 57.64$) was injected through each uterine artery into the spiral arterioles.

Follow-Up

All patients were given hormonal replacement therapy (Progyluton™, Bayer, Berlin, Germany) after receiving cell therapy. Endometrial cavity status was assessed by diagnostic hysteroscopy, vaginal ultrasound, and histology to determine the endometrial thickness and the presence or absence of endometrial adhesions before, 2, 3, and 6 months after cell therapy. Patients were then invited to undergo ART to attempt conception (FIG. 9).

Endometrial Immunohistochemistry

Blood vessels formation was assessed by CD31 & α-sma-Cy3 immunohistochemistry in paraffin sections using anti-human CD31 (Dako, Glostrup, Denmark) with a secondary Alexa goat anti-mouse 488, and mouse anti-human α-sma-Cy3 (Sigma-Aldrich, MO, EEUU). Slides were counterstained with DAPI (Invitrogen, CA, EEUU). Positive controls included human tonsil for CD31 and myometrium for α-sma. Slides were examined under a fluorescent Nikon Eclipse 80i microscope. Three separate 20× fields were used to analyze the total blood vessel formation per area by ImageJ Software. Data are presented as specific values for every patient before, and 3 months and 6 months after, cell therapy.

Statistical Analysis

Statistical analysis was performed using SPSS 17.0 software (IBM, MD, USA). A paired sample t-test was used to analyze the differences observed in the counting of total mature blood vessels. A p-value obtained in a 2-tailed test ≤0.05 was considered statistically significant.

Results

Two patients were initially excluded from the study due to poor mobilization of CD133+ cells (<40 million) in one case, and a lack of peripheral venous access in the other. A total of 16 patients completed the protocol. No major complications were reported.

Figure 7A:
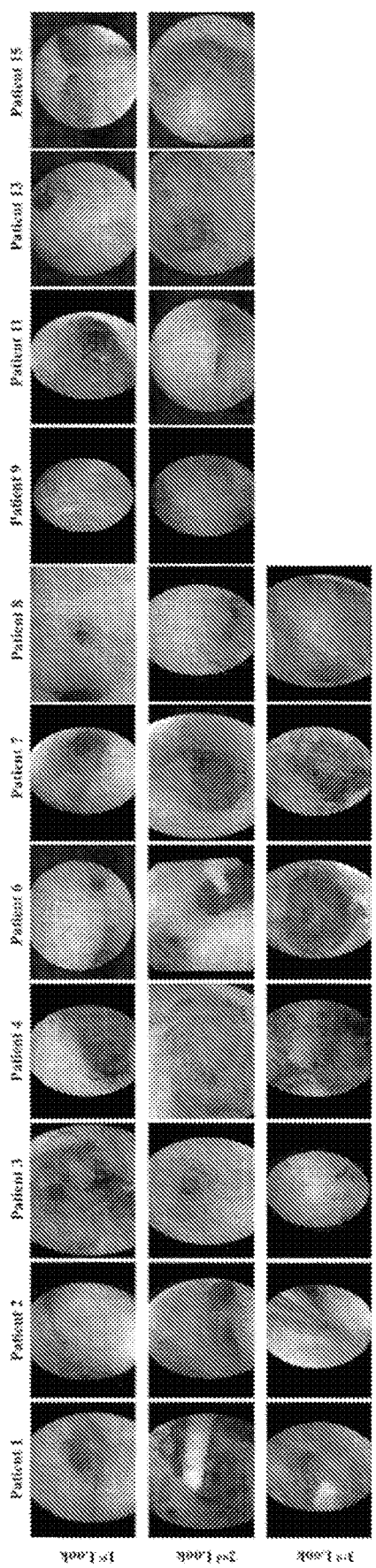
FIGS. 7A-7B show preoperative and postoperative hysteroscopic images. Histeroscopic findings in patients with Asherman's syndrome (FIG. 7A) or endometrial atrophy (FIG. 7B) before stem cell therapy (1st look), and 2-3 months (2nd look) and 4-6 months (3rd look) after stem cell therapy. The severity of the endometrial adhesions was graded according to the American Fertility Society classification.

Patients were referred to the study with a diagnosis of refractory AS (N=11) (Table 3). The patients' menstrual histories revealed amenorrhea in two patients and scant spotting in nine. The causes of AS were traumatic dilatation and curettage (D&C) (N=9), hysteroscopic myomectomy (N=1), and unexplained (N=1). The average number of previously attempted reparative operative hysteroscopies was two. No patient reported a significant improvement of her endometrial status despite surgical treatment. Three patients were classified as AS grade III, four patients were scored as grade II+EA, two patients were classified as grade II, and one patient was classified as AS grade I (FIG. 7A). The maximum endometrial thickness with high doses of HRT achieved prior to cell therapy was 4.3 mm±0.74 (ranging from 2.7-5 mm) (Table 3).

TABLE 3

Characteristics and Outcomes of Patients with Asherman's Syndrome

| Pt. | Preop MH | Etiology of AS | Prior repair attempts | Age | Max. preop ET | Hysteroscopy 1st look before cell therapy | 2nd look after cell therapy | 3rd look after cell therapy | Postop MH | Max. postop ET | Pregnancy Outcome |
|---|---|---|---|---|---|---|---|---|---|---|---|
| 1 | Scant spotting | D&C | h/s x 6 | 39 | 4.5 mm | AS Stage III | Stage II | Stage I | Regular with HRT | 5.2 mm | No |
| 2 | Scant spotting | D&C | None | 30 | 4 mm | AS Stage III | Stage II | Stage I | Regular with HRT | 6.5 mm | No |
| 3 | Scant spotting | D&C | h/s x 2 | 43 | 4.5 mm | AS Stage II | Stage I | Stage I | Regular with HRT | 7 mm | Yes, BP |
| 4 | Amenorrhea | D&C | h/s x 5 | 37 | 4.5 mm | EA + AS Stage II | Stage I | Stage I | Regular with HRT | 6.1 mm | No |
| 6 | Scant spotting | Unexplained | h/s x 1 | 45 | 5 mm | EA + AS Stage I | Stage I | Uterine cavity normalized | Regular with HRT | 5 mm | No |

TABLE 3-continued

Characteristics and Outcomes of Patients with Asherman's Syndrome

| Pt. | Preop MH | Etiology of AS | Prior repair attempts | Age | Max. preop ET | Hysteroscopy 1st look before cell therapy | Hysteroscopy 2nd look after cell therapy | Hysteroscopy 3rd look after cell therapy | Postop MH | Max. postop ET | Pregnancy Outcome |
|---|---|---|---|---|---|---|---|---|---|---|---|
| 7 | Scant spotting | D&C | h/s x 9 | 34 | 3.5 mm | EA + AS Stage II | Stage I | Stage I | Regular with HRT | | Yes, SP Premature Rupture of Membranes at 17 weeks |
| 8 | Amenorrhea | D&C; IUD (LNG 5 years) | h/s x 1 | 35 | 3.5 mm | EA + AS Stage II | Stage I | Stage I | Regular with HRT | 7.1 mm | No transfer. All abnormal embryos |
| 9 | Scant spotting | D&C | none | 40 | 4.7 mm | AS Stage III | Stage I | Not performed | Regular with HRT | 12 mm | No |
| 11 | Scant spotting | lm | h/s x 2 | 40 | 5 mm | AS Stage I | Stage I | Not performed | Regular with HRT | 6 mm | Yes, BP |
| 13 | Scant spotting | D&C; mm/t | None | 43 | 3 mm | EA + AS Stage II | Stage I | Not performed | Regular with HRT | 8 mm | Yes, EP |
| 15 | Scant spotting | D&C | h/s x 2 | 32 | 5 mm | AS Stage II | Uterine cavity normalized | Not performed | Regular with HRT | 6.8 mm | Yes, BP |

Figure 7B:
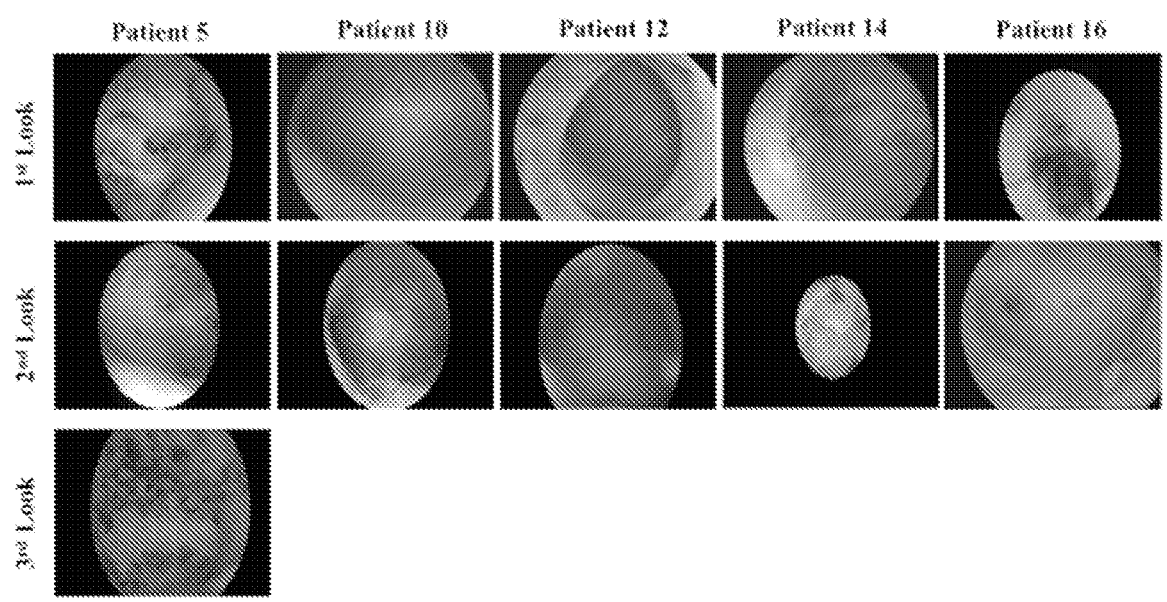

Note:
Pt = patient;
MH = menstrual history;
ET = endometrial thickness;
D&C = dilatation/curettage;
POF = premature ovarian failure;
h/s = hysteroscopy;
hm = hysteroscopic myomectomy;
lm = laparoscopic myomectomy;
AS = Asherman's syndrome (classified via American Fertility Society Classification of Intrauterine Adhesions, 1998);
EA = Endometrial Atrophy;
BP = Biochemical pregnancy;
EP = Ectopic Pregnancy;
SP = Spontaneous pregnancy;
ART = assisted reproductive treatment;
LNG = levonorgestrel;
HRT = Hormone Replacement Therapy Patients with EA and implantation failure (N=5) (Table 4) enrolled in this study had a previous menstrual history of amenorrhea (N=3) or scant spotting (N=2). The etiology was previous D&C (N=1), unexplained (N=1), the use of a levonorgestrel IUD (N=1), premature ovarian failure (N=1), and a previous hysteroscopic myomectomy (N=1). The average number of previous reparative operative hysteroscopies attempted was two. Severe endometrial atrophy was observed in all cases (FIG. 7B). The maximum endometrial thickness with high doses of HRT reached before cell therapy was 4.2 mm±0.8 (ranging from 2.7-5 mm) (Table 4).

TABLE 4

Characteristics and Outcomes of Patients with Endometrial Atrophy

| Pt. | Preop MH | Etiology of Atrophy | Prior repair attempts | Age | Max preop ET | Hysteroscopy 1st look before cell therapy | Hysteroscopy 2nd look after cell therapy | Hysteroscopy 3rd look after cell therapy | Postop MH | Max postop ET | Pregnancy Outcome |
|---|---|---|---|---|---|---|---|---|---|---|---|
| 5 | Scant spotting | hm | h/s x 3 | 42 | 5 mm | Endometrial Atrophy | Normal Endometrium | Normal Endometrium | Regular with HRT | 6.8 mm | No |
| 10 | Amenorrhea | D&C | h/s x 2 | 38 | 4 mm | Endometrial Atrophy | Normal Endometrium | Not performed | Regular with HRT | 7 mm | Yes, Clinical Miscarriage at 9 wks |
| 12 | Scant spotting | Unexplained | h/s x 2 | 35 | 4.3 mm | Endometrial Atrophy | Normal Endometrium | Not performed | Regular with HRT | 5.7 mm | Yes, Ongoing pregnancy |
| 14 | Amenorrhea | POF; IUD (LNG 2 years) | h/s x 1 | 30 | 2.7 mm | Endometrial Atrophy | Endometrial Atrophy | Not performed | Regular with HRT | 3.1 mm | No transfer for cell therapy failure |

TABLE 4-continued

Characteristics and Outcomes of Patients with Endometrial Atrophy

| Pt. | Preop MH | Etiology of Atrophy | Prior repair attempts | Age | Max preop ET | Hysteroscopy 1st look before cell therapy | 2nd look after cell therapy | 3rd look after cell therapy | Postop MH | Max postop ET | Pregnancy Outcome |
|---|---|---|---|---|---|---|---|---|---|---|---|
| 16 | Amenorrhea | POF | h/s x 1 | 41 | 5 mm | Endometrial atrophy | Uterine cavity normalized | Not performed | Regular with HRT | 5.7 mm | No |

Note:
Pt = patient;
MH = menstrual history;
ET = endometrial thickness;
D&C = dilatation/curettage;
POF = premature ovarian failure;
h/s = hysteroscopy;
hm = hysteroscopic myomectomy;
lm = laparoscopic myomectomy;
AS = Asherman's syndrome (classified via American Fertility Society Classification of Intrauterine Adhesions, 1998);
EA = endometrial atrophy;
BP = biochemical pregnancy;
EP = ectopic pregnancy;
SP = spontaneous pregnancy;
ART = assisted reproductive treatment;
LNG = levonorgestrel;
HRT = Hormone Replacement Therapy Endometrial Reconstruction after Stem Cell Therapy After autologous CD133$^+$ BMDSC therapy, menstrual cycles resumed with HRT in all 16 patients, except one with EA. However, the duration and intensity of menstruation, as assessed by the number of pads used, decreased progressively from a mean of 5.06 days (range, 3-7 days) in the first month to 2.12 (range, 1-3 days) in the sixth month after cell therapy (Supplemental FIG. 1A). Menstrual volume also decreased from a mean of 2.68 (range, 1-5) to 1.5 (range, 1-4) pads per day in the sixth month.

Uterine observations performed 2, 3, and 6 months after cell therapy revealed improvements in the endometrium and the uterine cavity (Tables 3 & 4; FIG. 7). Specifically, all patients diagnosed with stage III AS improved to stage I, while one of the two patients affected with stage II showed a completely normalized endometrial cavity and the other improved to stage I. The remaining patient, initially diagnosed as stage I, improved with respect to the qualifying score as shown in Table 3. The maximum postoperative endometrial thickness obtained was 6.7 mm (range, 3.1-12 mm) (Table 3, FIG. 7A). In the EA group, a normal endometrium was observed after cell therapy in four out of the five patients (Table 4; FIG. 7B). The maximum endometrial thickness obtained after cell therapy was 5.7 mm (range, 5-12 mm) (Table 4).

The total number of mature blood vessels formed were assessed in 8 patients by the co-localization of CD31 and α-sma performed before, and 3 and 6 months after, cell therapy (FIG. 8). An incremental increase of blood vessel formation was observed after 3 months of treatment (patients 4, 5, 7, 12, and 13), while a consistent number of mature blood vessels were found in others (patients 6, 9, and 10) (FIG. 8H). To compare the results between the starting point of the experiment (referred to as the control) and 3 months after the specific treatment with CD133+ cells, the corresponding averages and SEMs of the data were examined. An increased number of total mature blood vessels (CD31+/α-sma+) was observed in patients after three months of treatment (p=0.021). These results suggest a characteristic neoangiogenesis after autologous injection of CD133+ cells in patients with AS and EA that progressively diminishes after 6 months (FIG. 8I).

Functionality of the reconstructed endometrium was assessed by the reproductive outcome of patients wishing to conceive after autologous CD133+BMDSCs therapy (Tables 3 & 4). Two patients became pregnant spontaneously, two and four months after cell therapy, respectively, resulting in an ongoing pregnancy (patient 15), and a miscarriage during the 17$^{th}$ week due to a premature rupture of the membranes (patient 7). Six positive pregnancies were obtained after 13 embryo transfers, resulting in three biochemical pregnancies, one miscarriage at the ninth week due to a chromosomally abnormal embryo assessed after miscarriage, one ectopic pregnancy, and one ongoing pregnancy (patient 12). In one case, the embryo transfer was cancelled due to chromosomal abnormalities in all of the embryos (patient 8) and in another case, transfer was not performed due to the failure of cell therapy (patient 14).

Discussion

From a histological point of view, AS corresponds to a replacement of the endometrial stroma by fibrous tissue affecting the endometrial stem cells and, therefore, the tissue function. Glands are usually replaced by an inactive cubocolumnar epithelium that is generally non-responsive to hormonal stimulation and causes the complete disappearance of the endometrial structure affecting the niche of endometrial stem cells and, therefore, the tissue function. During the first 50 to 60 years after the discovery of AS, researchers focused on the prevalence, etiology, and pathology of the condition. With the advent of endoscopy, new methods for the diagnosis and treatment of the condition were developed; however, despite the technological advances, about 50% of the AS cases today have no comprehensive cure.

Here, the first instance of stem cell therapy specifically targeting the endometrial stem cell niche is described. Under steady state conditions, circulating EPCs (cEPs) represent only 0.01% of cells in the circulation. Therefore, mobilization of cEPs coupled with direct infusion in the affected organ was planned. Autologous CD133$^+$ BMDSCs were isolated after mobilization with G-CSF and then reintroduced into the spiral arterioles of the patient's uterus using non-invasive radiological procedures. CD133+ BMDSCs regenerate vascularization and induce endometrial proliferation, leading to the creation of an autologous reconstructed endometrium. CD133+ BMDSCs have recently been explored in clinical trials for regenerative medicine in non-hematological applications.

The primary objective was the reconstruction of the endometrium, assessed first by the resumption of menstruation, which occurred in 15 out of 16 of our patients. Although the duration and intensity of menstruation decreased progressively six months after cell therapy, stem cell therapy made an immediate difference in endometrial morphology. Hysteroscopical visualization of the uterine cavity, endometrial thickness measured by vaginal ultrasound, and neoangiogenesis through immunohistochemistry were consistent with an effective, although transitory, reconstruction of the endometrium. The secondary objective was to test the functionality of the reconstructed endometrium by attempting conception. Several spontaneous pregnancies, with the use of ART, were achieved after cell therapy, and the two miscarriages observed in this study were not related to endometrial functionality.

Cell engraftment was the main concern because the IRB would not allow labeling of CD133+BMDSCs with superparamagnetic iron-oxide nanoparticles (SPIOs) to track the injected cells. Instead, a murine immunodeficient experimental model for Asherman's syndrome was utilized for this purpose. An aliquot of 1 million CD133+ BMDSCs from patients involved in the study was used for further characterization and assayed for Lgr5+ cells and aldehyde dehydrogenase1 (ALDH1) activity, resulting in 75.72±8% Lgr5+ cells and 77.45±7.81% ALDH1 activity, identifying stem and progenitor cell status, respectively. Another 1 million cells aliquot was incubated with 50 µg/mL Molday ION Rhodamine B for 18 h resulting in a labeling efficiency greater than 97% in all experiments. Then, SPIO-labeled cells were injected in an immunodeficient mouse model of Asherman's syndrome through a tail vein or intrauterine injection. Cell engraftment was detected by the identification of intracellular iron deposits using Prussian blue staining, revealing that CD133+ BMDSCs engrafted predominantly around endometrial blood vessels of the traumatized endometrium.

A previous case report showed positive results treating AS with the autologous stem cell isolation of CD9, CD40, and CD90 cells from bone marrow and placing them into the endometrial cavity, while another case report described the direct placement of non-characterized mononuclear stem cells into the subendometrial zone with a needle. Both case reports differ in the type of cells delivered and stem cell niche targeted.

The present study demonstrates that CD133+ BMDSC autologous cell therapy is useful in treating patients with refractory AS and EA wishing to conceive.

REFERENCES

1. Cha J, Vilella F, Dey S K and Simon C. "Molecular Interplay in Successful Implantation" in Ten Critical Topics in Reproductive Medicine, S. Sanders. Science/AAAS, Washington, DC, 2013, pp. 44-48.
2. Cervello I, Gil-Sanchis C, Mas A, Delgado-Rosas F, Martinez-Conejero J A, Galan A, Martinez-Romero A, Martinez S, Navarro I, Ferro J, Horcajadas J A, Esteban F J, et al. Human endometrial side population cells exhibit genotypic, phenotypic and functional features of somatic stem cells. PLoS ONE 2010; 5:e10964.
3. Cervello I, Mas A, Gil-Sanchis C, Peris L, Faus A, Saunders P T, Critchley H O, Simon C. Reconstruction of endometrium from human endometrial side population cell lines. PLoS ONE 2011; 6:e21221.
4. Masuda H, Matsuzaki Y, Hiratsu E, Ono M, Nagashima T, et al. (2010) Stem cell-like properties of the endometrial side population: implication in endometrial regeneration. PLoS One. 5(4):e10387.
5. Pittenger M F, Mackay A M, Beck S C, Jaiswal R K, Douglas R, et al. (1999) Multilineage potential of adult human mesenchymal stem cells. Science 284 (5411):143-7.
6. Taylor H S. (2004) Endometrial cells derived from donor stem cells in bone marrow transplant recipients. JAMA. 292(1):81-5.
7. Du H, Taylor H S. (2007) Contribution of bone marrow-derived stem cells to endometrium and endometriosis. Stem Cells 25(8):2082-6.
8. Mints M, Jansson M, Sadeghi B, Westgren M, Uzunel M, et al. (2008) Endometrial endothelial cells are derived from donor stem cells in a bone marrow transplant recipient. Hum Reprod. 23(1):139-43.
9. Ikoma T, Kyo S, Maida Y, Ozaki S, Takakura M, et al. (2009) Bone marrow-derived cells from male donors can compose endometrial glands in female transplant recipients. Am J Obstet Gynecol. 201(6):608.e1-8.
10. Cervello I, Gil-Sanchis C, Mas A, Faus A, Sanz J, Moscardo F, Higueras G, Sanz M A, Pellicer A, Simon C. Bone marrow-derived cells from male donors do not contribute to the endometrial side population of the recipient. PLoS ONE 2012; 7:e30260.
11. Du H, Taylor H S. Contribution of bone marrow-derived stem cells to endometrium and endometriosis. Stem Cells 2007; 25:2082-2086.
12. Brantincsak A, Brownstein M J, Cassiani-Ingoni R, Pastorino S, Szalayoval, Toth Z E, Key S, Nemeth K, Pickel J, Mezey E. CD45-positive blood cells give rise to uterine epithelial cells in mice. Stem Cells 2007; 25: 2820-2826.
13. Zhou Y, Gan Y, Taylor H S. Cigarette smoke inhibits recruitment of bone marrow-derived stem cells to the uterus. Reprod Toxicol 2011; 31:123-127.
14. Du H, Naqvi H, Taylor H S. Ischemia/reperfusion injury promotes and granulocyte-colony stimulating factor inhibits migration of bone marrow derived stem cells to endometrium. Stem Cells Dev 2012; 21:3324-3331.
15. Morelli S, Rameshwar P and Goldsmith L T. Experimental Evidence for Bone Marrow as a Source of Non-hematopoietic Endometrial Stromal and Epithelial Compartment Cells in a Murine Model. Biol Reprod 2013; 89:7, 1-7.
16. Aghajanova L, Horcajadas J A, Esteban F J, Giudice L C. The bone marrow derived human mesenchymal stem cell: potential progenitor of the endometrial stromal fibroblast. Biol Reprod 2010; 82:1076-1087.
17. Urbich C and Dimmeler S. Endothelial Progenitor Cells: Characterization and Role in Vascular Biology. Circ Res. 2004; 95:343-353
18. Yu D, Wong Y M, Cheong Y, Xia E, Li T C. Asherman syndrome—one century later. Fertil Steril 2008; 89:759-79.
19. Ravina J H, Herbreteau D, Ciraru-Vigneron N, et al. Arterial embolisation to treat uterine myomata. Lancet 1995; 346(8976):671-2.

20. Chaitanya B Nagori, Sonal Y Panchal, and Himanshu Patel. Endometrial regeneration using autologous adult stem cells followed by conception by in vitro fertilization in a patient of severe Asherman's syndrome. J Hum Reprod Sci; 4(1): 43-48 (2011)
21. Gargett C E, Healy D L. Generating receptive endometrium in Asherman's syndrome. J Hum Reprod Sci, 4(1): 49-52 (2011)
22. Bradley E A, Reidy J F, Forman R G, Jarosz J, Braude P R. Transcatheter uterine artery embolisation to treat large uterine fibroids. Br J Obstet Gynaecol 1998; 105 (2):235-40
23. Dmowski W P, Greenblatt R B. Asherman's syndrome and risk of placenta accreta. Obstet Gynecol 1969; 34: 288-299.
24. Ventolini G, Zhang M, Gruber J. Hysteroscopy in the evaluation of patients with recurrent pregnancy loss: a cohort study in a primary care population. Surg Endosc 2004; 18: 1782-1784.
25. Senturk L M, Erel C T. Thin endometrium in assisted reproductive technology. Curr Opin Obstet Gynecol. 2008; 20:221-228.
26. Sher G, Fisch J D. Effect of vaginal sildenafil on the outcome of in vitro fertilization (IVF) after multiple IVF failures attributed to poor endometrial development. Fertil Steril 2002; 78: 1073-6.
27. Okusami A A, Moore M E, Hurwitz J M, Richlin S S. A case series of patients with endometrial insufficiency treatment with pentoxifylline and alphatocopherol. Fertil Steril 2007; 88: S200.
28. Brantincsak A, Brownstein M J, Cassiani-Ingoni R, et al. CD45-positive blood cells give rise to uterine epithelial cells in mice. Stem Cells 2007; 25: 2820-2826.
29. Rafii S, Lyden D. Therapeutic stem and progenitor cell transplantation for organ vascularization and regeneration. Nat Med. 2003; 9: 702-12.
30. Uchida N, Buck D W, He D, et al. Direct isolation of human central nervous system stem cells. Proc Natl Acad Sci 2000; 97: 14720-14725.
31. Sagrinati C, Netti G S, Mazzinghi B, et al. Isolation and characterization of multipotent progenitor cells from the Bowman's capsule of adult human kidneys. J Am Soc Nephrol 2006; 17: 2443-2456.
32. Richardson G D, Robson C N, Lang S H, Neal D E, Maitland N J, Collins A T. CD133, a novel marker for human prostatic epithelial stem cells. J Cell Sci 2004; 117: 3539-3545.
33. Kordes C, Sawitza I, Müller-Marbach A, et al. CD133+ hepatic stellate cells are progenitor cells. Biochem Biophys Res Commun 2007; 352: 410-417.
34. The American Fertility Society classifications of adnexal adhesions, distal tubal occlusion, tubal occlusion secondary to tubal ligation, tubal pregnancies, Mullerian anomalies and intrauterine adhesions. Fertil Steril 1988; 49: 944-55.
35. Gordon P R, Leimig T, Babarin-Dorner A, et al. Large-scale isolation of CD133+ progenitor cells from G-CSF mobilized peripheral blood stem cells. Bone Marrow Transpl 2003; 31: 17-22.
36. Goodwin S C, Spies J B, Worthington-Kirsch R, et al. Uterine artery embolization for treatment of leiomyomata: long-term outcomes from the FIBROID Registry. Obstet Gynecol. 2008; 111(1):22-33.
37. Cervello I, Gil-Sanchis C, Santamaría X, Cabanillas S, Díaz A, Faus A, Pellicer A, Simón C. Human bone marrow-derived stem cells improve endometrial regeneration in a murine experimental Asherman's syndrome model. Human Reprod 2015, in press.
38. Asherman J G. Amenorrhoea traumatica (atretica). J Obstet Gynaecol Br Emp 1948; 55: 23-30.
39. Donnez J, Nisolle M. Hysteroscopic lysis of intrauterine adhesions (Asherman' syndrome). In Donnez J (ed): Atlas of laser operative laparoscopy and hysteroscopy. New York: Press-Parthernon Publishers 1994:3-12.
40. March C M, management of Ashermans Syndrome. Reprod Biomed Online 2011 (1):63-76
41. Singh N, Mohanty S, Seth T, Shankar M, Bhaskaran S, Dharmendra S. Autologous stem cell transplantation in refractory Asherman's syndrome: A novel cell based therapy. J Hum Reprod Sci 2014; 7: 93-8.

Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A method to induce endometrial regeneration, comprising:
administering an effective amount of autologous CD133$^+$ bone marrow derived stem cells (BMDSC) into the uterine spiral arterioles of a subject in need thereof to induce endometrial regeneration, wherein the autologous CD133+ BMDSCs are obtained from peripheral blood of the subject by administering to the subject an agent to mobilize BMDSCs from bone marrow into peripheral blood of the subject; and isolating CD133$^+$ BMDSC from the peripheral blood of the subject using an anti-CD133 antibody.

2. The method of claim 1, wherein the subject is known to have Asherman's syndrome or endometrial atrophy.

3. The method of claim 2, wherein the subject has endometrial atrophy that is resistant to hormonal treatment.

4. The method of claim 1, wherein the subject has had one or more prior embryo implantation failures.

5. The method of claim 1, wherein the agent to mobilize BMDSC is granulocyte colony-stimulating factor (G-CSF).

6. The method of claim 1, wherein the CD133$^+$ BMDSC are isolated from the peripheral blood of the subject by apheresis using an anti-CD133 antibody.

7. The method of claim 1, wherein the CD133$^+$ BMDSC are administered into the uterine spiral arterioles through a catheter.

8. The method of claim 1, wherein the CD133+ BMDSC are labeled with superparamagnetic iron-oxide nanoparticles (SPIOs).

9. The method of claim 1, wherein the effective amount of autologous CD133$^+$ bone marrow derived stem cells is at least 45 million cells.

10. The method of claim 1, wherein the effective amount of autologous CD133$^+$ bone marrow derived stem cells is at least 50, 55, 60, or 65 million cells.

11. A method to induce endometrial regeneration, comprising:
administering to the subject an agent to mobilize BMDSCs from bone marrow into peripheral blood of the subject;
isolating autologous CD133$^+$ bone marrow derived stem cells (BMDSC) from the peripheral blood of a subject in need thereof using an anti-CD133 antibody; and
administering an effective amount of the isolated CD133$^+$ BMDSC into the uterine spiral arterioles of the subject to induce endometrial regeneration.

12. The method of claim 11, wherein granulocyte colony-stimulating factor (G-CSF) is administered to the subject before isolating the CD133$^+$ BMDSC.

13. The method of claim 11, wherein the CD133$^+$ BMDSC are isolated from the peripheral blood of the subject by apheresis using an anti-CD133 antibody.

14. The method of claim 11, wherein the CD133$^+$ BMDSC are administered into the uterine spiral arterioles through a catheter.

15. The method of claim 11, wherein the subject is known to have Asherman's syndrome or endometrial atrophy.

16. The method of claim 15, wherein the subject has endometrial atrophy that is resistant to hormonal treatment.

17. The method of claim 11, wherein the subject has had one or more prior embryo implantation failures.

18. The method of claim 11, wherein the CD133+ BMDSC are labeled with superparamagnetic iron-oxide nanoparticles (SPIOs).

19. The method of claim 11, wherein the effective amount of the autologous CD133$^+$ bone marrow derived stem cells is at least 45 million cells.

20. The method of claim 11, wherein the effective amount of the autologous CD133$^+$ bone marrow derived stem cells is at least 50, 55, 60, or 65 million cells.

\* \* \* \* \*